United States Patent
Muhlenberg et al.

(10) Patent No.: US 7,024,244 B2
(45) Date of Patent: Apr. 4, 2006

(54) ESTIMATION OF STROKE VOLUME CARDIAC OUTPUT USING AN INTRACARDIAC PRESSURE SENSOR

(75) Inventors: Lambert Muhlenberg, Landgraaf (NL); Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 373 days.

(21) Appl. No.: 10/126,733

(22) Filed: Apr. 22, 2002

(65) Prior Publication Data

US 2003/0199779 A1 Oct. 23, 2003

(51) Int. Cl.
*A61N 1/365* (2006.01)

(52) U.S. Cl. .......................... 607/23; 607/24

(58) Field of Classification Search ........ 600/485–486, 600/488, 513, 526; 607/9, 23–24
See application file for complete search history.

(56) References Cited

U.S. PATENT DOCUMENTS

| | | | |
|---|---|---|---|
| 4,316,472 A | 2/1982 | Mirowski et al. | 607/9 |
| 4,375,817 A | 3/1983 | Engle et al. | 607/4 |
| 4,379,479 A | 4/1983 | Whiting | 160/201 |
| 4,384,585 A | 5/1983 | Zipes | 607/5 |
| 4,476,868 A | 10/1984 | Thompson | 607/14 |
| 4,566,063 A | 1/1986 | Zolnowsky | 712/241 |
| 4,577,633 A | 3/1986 | Berkovits et al. | 607/15 |
| 4,587,970 A | 5/1986 | Holly et al. | 607/15 |
| 4,708,143 A * | 11/1987 | Schroeppel | 607/23 |
| 4,727,877 A | 3/1988 | Kallok | 607/5 |
| 4,800,883 A | 1/1989 | Winstrom | 607/7 |
| 4,821,723 A | 4/1989 | Baker et al. | 607/7 |
| 4,880,005 A | 11/1989 | Pless et al. | 607/15 |
| 4,949,719 A | 8/1990 | Pless et al. | 607/7 |
| 4,953,511 A | 9/1990 | Boah et al. | 122/18.4 |
| 5,099,838 A | 3/1992 | Bardy | 607/2 |
| 5,117,824 A | 6/1992 | Keimel et al. | 607/4 |
| 5,131,388 A | 7/1992 | Pless | 607/5 |
| 5,144,949 A | 9/1992 | Olson et al. | 607/17 |
| 5,158,078 A | 10/1992 | Bennet et al. | 607/27 |
| 5,163,427 A | 11/1992 | Keimel | 607/5 |
| 5,188,105 A | 2/1993 | Keimel | 607/5 |

(Continued)

FOREIGN PATENT DOCUMENTS

WO    WO 00/51495    9/2000

OTHER PUBLICATIONS

"Automatic Tachycardia Recognition" by Arzbaecher et al. PACE May-Jun. 1984, pp. 541-547.

*Primary Examiner*—Carl Layno
(74) *Attorney, Agent, or Firm*—Paul H. McDowall; Girma Wolde-Michael

(57) ABSTRACT

Techniques are described for estimating a rate of blood flow from a heart, such as a stroke volume or a cardiac output, as a function of a pressure in the heart. A pressure monitor may measure pressure values, and identify the times at which pressure values and valve opening and closing occur. The pressure monitor may estimate a velocity-time function as a function of the measured pressures and identified times, and may calculate a velocity-time integral by integrating the velocity-time function. The pressure monitor may also calculate an estimated velocity-time integral directly as a function of the measured pressures and the identified times. The pressure monitor may calculate the stroke volume or cardiac output using the velocity-time integral. The pressure monitor may control a delivery of therapy by an implantable medical device as a function of the stroke volume or cardiac output.

29 Claims, 11 Drawing Sheets

U.S. PATENT DOCUMENTS

| | | | |
|---|---|---|---|
| 5,188,106 A * | 2/1993 | Nappholz et al. | 607/24 |
| 5,199,428 A | 4/1993 | Obel et al. | 607/44 |
| 5,207,218 A | 5/1993 | Carpenter et al. | 607/36 |
| 5,269,298 A | 12/1993 | Adams | 607/5 |
| 5,287,753 A | 2/1994 | Routh et al. | 73/861.25 |
| 5,289,823 A * | 3/1994 | Eckerle | 600/492 |
| 5,312,453 A | 5/1994 | Shelto et al. | 607/19 |
| 5,314,430 A | 5/1994 | Bardy | 607/5 |
| 5,330,507 A | 7/1994 | Schwortz | 607/14 |
| 5,331,966 A | 7/1994 | Bennet et al. | 600/508 |
| 5,354,316 A | 10/1994 | Keimel | 607/15 |
| 5,368,040 A | 11/1994 | Carney | 600/513 |
| 5,409,009 A * | 4/1995 | Olson | 600/454 |
| 5,535,752 A | 7/1996 | Halperin et al. | 600/483 |
| 5,545,186 A | 8/1996 | Olson et al. | 607/14 |
| 5,564,434 A | 10/1996 | Halperin et al. | 600/488 |
| 5,606,972 A | 3/1997 | Routh | 600/455 |
| 5,626,623 A | 5/1997 | Kieval et al. | 607/23 |
| 5,634,465 A | 6/1997 | Schmiesing et al. | 600/454 |
| 5,690,886 A | 11/1997 | Kurihara | 264/328 |
| 5,797,395 A | 8/1998 | Martin | 600/486 |
| 5,800,464 A * | 9/1998 | Kieval | 607/9 |
| 5,810,735 A | 9/1998 | Halperin et al. | 600/486 |
| 5,868,676 A | 2/1999 | McCabe et al. | 600/454 |
| 6,217,522 B1 | 4/2001 | Shoshan | 600/490 |
| 6,314,323 B1 * | 11/2001 | Ekwall | 607/23 |
| 6,754,532 B1 * | 6/2004 | Ferek-Petric | 607/17 |

* cited by examiner

ESTIMATION OF STROKE VOLUME CARDIAC OUTPUT USING AN INTRACARDIAC PRESSURE SENSOR

FIELD OF THE INVENTION

The present invention relates generally to cardiac monitoring, and more particularly to the monitoring of rates of blood flow from the heart, such as stroke volume and cardiac output.

BACKGROUND

Stroke volume and cardiac output are measures of the performance of a heart, and thus are very important to physicians. Stroke volume is the volume of blood pumped out of the heart in one beat. Cardiac output is the volume of blood pumped out of the heart in one minute. Physicians may use stroke volume and cardiac output measurements for evaluating and monitoring cardiac function in patients with congestive heart failure or other cardiovascular maladies. Stroke volume and cardiac output are also used for diagnosis and to guide therapeutic decisions.

One conventional technique for estimating cardiac output is sometimes referred to as the Fick method. This technique involves having a patient breathe pure $O_2$, and measuring the $O_2$ uptake directly from the net blood gas flux and measuring the blood oxygen content via venous and arterial blood samples. The blood samples can be taken with two catheters, one located in an artery, such as the brachial artery, and another located in a vein, such as the femoral vein. While this method may yield an accurate estimation of cardiac output, the disadvantages of this method include an inability to make continuous real-time measurements, and that the measurements necessarily occur in a hospital or clinic. Additionally, the measurements may not be continuously repeated due to the invasiveness of the method and the significant amount of blood required for each measurement.

Another existing method for measuring cardiac output is the indicator dilution or thermo-dilution technique, which involves the injection of a predetermined amount of an indicator dye or relatively cool saline solution into the right atrium. The dilution of the dye or the temperature and conductivity of the saline is measured downstream. The average volume of blood flow is inversely proportional to the integrated area under the measured dilution curve. The main disadvantage of indicator dilution is that it does not allow continuous estimation of cardiac output because recirculation of dye through the bloodstream corrupts subsequent measurements. Thermo-dilutions also may not be repeated for a long period of time because it dilutes the patient's blood supply. Additionally, these methods provide only average values and occur only in a hospital or clinic setting.

One commonly used existing method for continuously estimating stroke volume and cardiac output involves the use of echocardiography. Using echo-Doppler ultrasound equipment, the velocity of the blood as it travels through an outflow tract during a heartbeat may be measured. These velocity measurements form velocity-time curves. Stroke volume may be continuously estimated as a function of the results of integration of measured velocity-time curves. Cardiac output may be calculated using the estimated stroke volume value. Although echocardiography produces an accurate estimation of stroke volume and cardiac output, this method requires bulky ultrasound equipment that restricts its use to hospitals and clinics.

Other continuous estimation methods include techniques involving the use of impedance measurements to detect changes in blood volume, and techniques involving acute measurement of the blood flow from the heart with a flow probe. Neither of these methods, nor any of the above-discussed methods, allows for continuous estimation of stroke volume or cardiac output in an outpatient setting via an implantable device. Because the condition of a patient may change between visits to a physician, and because these changes in condition between visits may be of use to the physician when he or she is making future therapeutic decisions, it is desirable to monitor the patient's stroke volume or cardiac output continuously in an outpatient setting.

One existing method for continuously estimating cardiac output as a function of pressure measured in a heart is disclosed in U.S. Pat. No. 5,797,395, issued to Martin. The method disclosed in the Martin patent involves the measurement of an aortic pressure wave with a catheter inserted in the radial artery. The characteristics of the measured pressure wave are then compared to characteristics of pressure waves with known cardiac output values to determine a match and to thus determine a cardiac output value for the measured pressure wave. The disadvantages of this method are that it is not applicable to an outpatient setting, and that it requires substantial and complex processing in order to yield an accurate result.

Because these changes in condition may reflect or lead to a sudden deterioration of the patient's condition, particularly in the case of patients with congestive heart failure, it may be desirable to continuously adjust a therapy in an outpatient setting as a function of the estimated stroke volume or cardiac output. These adjustments to the therapy may avert deterioration in condition between office visits, and thus the patient may avoid a possible hospitalization or death. One existing method for continuously estimating cardiac output in an outpatient setting as a function of pressure measured in a heart, and adjusting cardiac pacing parameters as a function of the estimated cardiac output is disclosed in U.S. Pat. No. 6,314,323 B1, issued to Ekwall. The Ekwall patent discloses estimating cardiac output by integrating a ventricular pressure curve between a time of valve opening and a time of valve closing. A disadvantage of this method is that it requires complex processing of the pressure signal in order to estimate cardiac output. Thus, the complexity, expense, and power consumption of an implantable device that utilizes this method to estimate cardiac output may be increased.

Examples of the above referenced existing techniques and/or devices for determining stroke volume and cardiac output, and existing techniques for measuring the pressure of blood in a heart may be found in the issued U.S. Patents listed in Table 1 below.

TABLE 1

| Patent No. | Inventor | Issue Date |
| --- | --- | --- |
| 6,325,762 | Tjin | Dec. 04, 2001 |
| 6,314,323 B1 | Ekwall | Nov. 06, 2001 |
| 6,217,522 B1 | Shoshan | Apr. 17, 2001 |
| WO 00/51495 | Buck et al. | Sep. 08, 2000 |
| 5,868,676 | McCabe et al. | Feb. 09, 1999 |
| 5,810,735 | Halperin et al. | Sep. 22, 1998 |
| 5,797,395 | Martin | Aug. 25, 1998 |
| 5,626,623 | Kievel et al. | May 06, 1997 |
| 5,606,972 | Routh | Mar. 04, 1997 |
| 5,535,752 | Halperin et al. | Jul. 16, 1996 |

TABLE 1-continued

| Patent No. | Inventor | Issue Date |
|---|---|---|
| 5,368,040 | Carney | Nov. 29, 1994 |
| 5,287,753 | Routh et al. | Feb. 22, 1994 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to estimating stroke volume or cardiac output. Such problems may include, for example, the inability of existing methods to continuously and accurately estimate stroke volume or cardiac output on a beat-to-beat basis in an outpatient setting. Such problems may also include the complexity of existing methods to estimate stroke volume and cardiac output on a beat-to-beat basis in an outpatient setting. It is an object of the present invention to provide a system and method to continuously and more accurately estimate stroke volume or cardiac output on a beat-to-beat basis in an outpatient setting. It is a further object of the present invention to provide a less resource intensive system and method to estimate stroke volume or cardiac output on a beat-to-beat basis in an outpatient setting. In particular, it is an object of the present invention to continuously estimate stroke volume or cardiac output on a beat-to-beat basis as a function of a pressure in a heart using an implantable pressure monitor.

The present invention has certain features. In particular, various embodiments of the present invention may include a pressure monitor that monitors a pressure in a heart and estimates a stroke volume or a cardiac output as a function of the pressure. The pressure monitor may receive a pressure signal representative of the pressure within the heart from a pressure sensor.

The pressure monitor may comprise a processor that estimates the stroke volume or cardiac output as a function of the pressure signal. The processor may calculate a change in the monitored pressure, and estimate the stroke volume or the cardiac output as a function of the change. The processor may identify a pressure at a time of valve opening and a peak pressure, and may calculate the change in the pressure as the difference between these identified pressures.

In various embodiments of the present invention, the processor may also identify a time of valve opening, a time of peak pressure and a time of valve closing. In some embodiments of the present invention, the processor may measure a duration of a time period between the time of valve opening and the time of valve closing and estimate the stroke volume and the cardiac output as a function of the duration. In various embodiments of the present invention, the processor may estimate a velocity-time integral value as a function of the calculated change in the pressure and the duration.

In various embodiments of the present invention, the processor may estimate velocity data as a function of the calculated change in pressure. The velocity data may include a peak velocity, which the processor may estimate as a function of the change in pressure. The processor may also estimate the velocity data as a function of the identified time of valve opening, time of peak pressure, and time of valve closing. The velocity data may comprise an estimated velocity-time function. The processor may integrate the velocity data and estimate stroke volume or cardiac output as a function of a result of the integration.

The processor may also receive an electrical activity signal representative of the electrical activity within the heart via an electrode placed within the heart. The processor may calculate a heart rate as a function of the electrical activity signal. The processor may use the heart rate to estimate cardiac output.

In various embodiments of the present invention, the stroke volume or cardiac output estimated by the processor may be output by the processor to a physician via output circuitry, such as RF telemetry or remote distribution circuitry, and a programmer. In various embodiments of the present invention, the processor may store the estimated stroke volume or cardiac output in memory for later retrieval.

In some embodiments of the present invention, the processor may also control the delivery of therapy by an implantable medical device as a function of the estimated stroke volume or cardiac output. In some embodiments of the invention, the implantable medical device may be a pacemaker or an implantable drug pump.

The present invention has certain advantages. That is, in comparison to known implementations for estimating stroke volume or cardiac output, various embodiments of the present invention may provide one or more advantages. Such advantages may include, for example, continuous and more accurate or less resource intensive estimation of stroke volume or cardiac output on a beat-to-beat basis in an outpatient setting.

For example, the system and method of the present invention may be realized in an implantable pressure monitor. Thus, the pressure monitoring and stroke volume or cardiac output estimation may occur in an outpatient setting. Further, the processor may calculate the change in pressure and identify the times on a beat-to-beat basis, thus continuous beat-to-beat estimation of stroke volume or cardiac output by the processor is possible. Additionally, the present system and method for estimating stroke volume or cardiac output may achieve these advantages while maintaining a similar level of accuracy to that of other methods, such as echocardiography.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
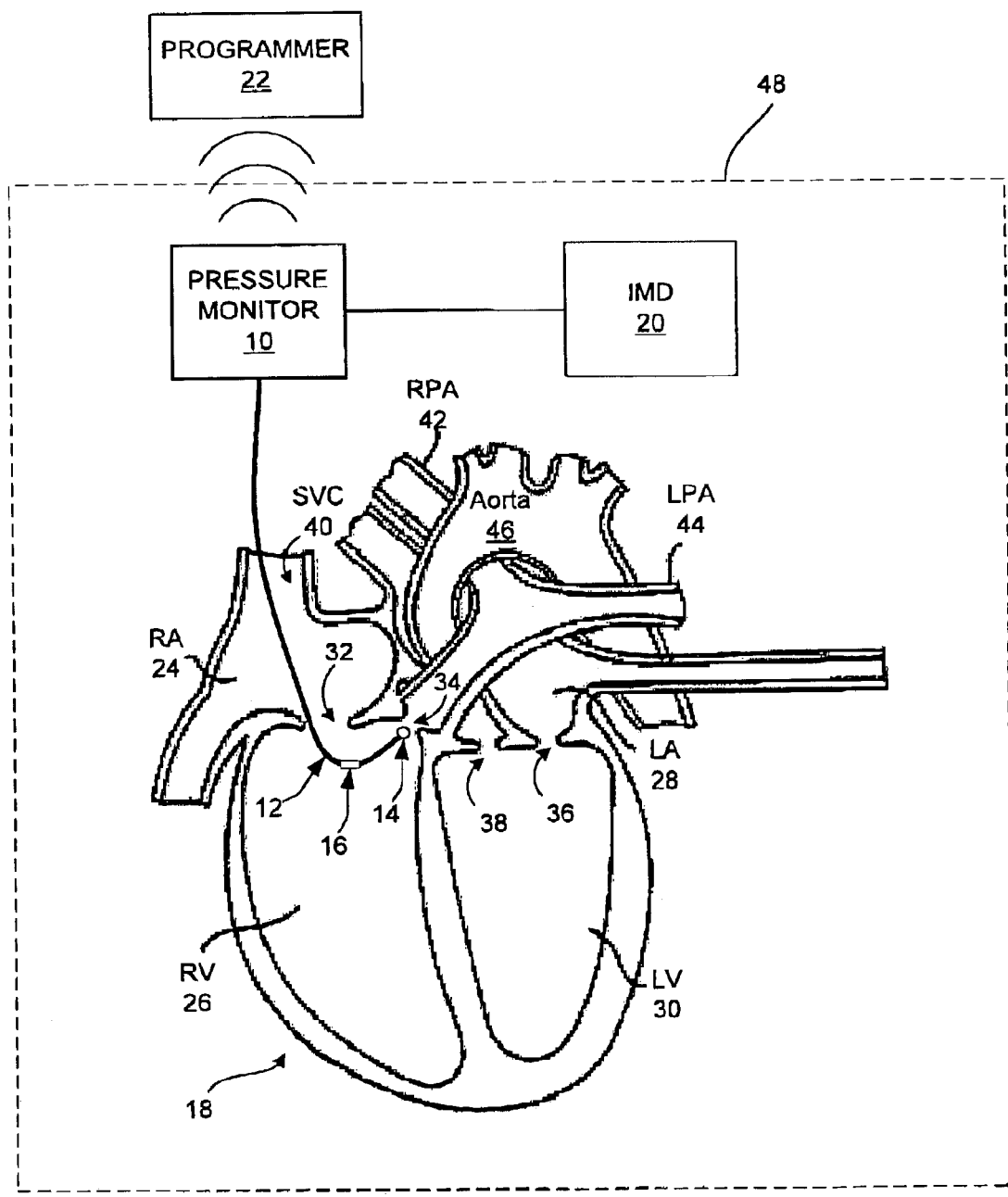
FIG. 1 is a schematic diagram illustrating an implantable medical device coupled to a pressure monitor that estimates a rate of blood flow, such as a stroke volume or a cardiac output, from a heart as a function of a pressure in the heart.

The present invention provides a system and method to estimate a rate of blood flow from the heart, such as a stroke volume or a cardiac output, as a function of a sensed pressure in a heart. FIG. 1 is a schematic diagram illustrating a pressure monitor 10 that estimates a rate of blood flow, such as a stroke volume or a cardiac output, from heart 18 as a function of the pressure in heart 18 in accordance with the present invention.

Pressure monitor 10 is coupled to a pressure sensor 14 by a lead 12. Pressure sensor 14 senses the fluid pressure in heart 18. Pressure sensor 14 may generate a pressure signal itself, or may modulate a pressure signal conducted through lead 12 as a function of the fluid pressure in heart 18. Pressure monitor 10 receives, monitors and analyzes the pressure signal, and estimates stroke volume, cardiac output, or both as a function of the pressure signal, as will be described in more detail below.

Pressure sensor 14 may be one of many forms of pressure sensors. One form of pressure sensor that is useful for measuring blood pressure inside a human heart is a capacitive absolute pressure sensor, as described in U.S. Pat. No. 5,564,434 to Halperin, et al., hereby incorporated by reference herein in its entirety. Pressure sensor 14 may also be a piezoelectric crystal or piezoresistive pressure transducer. The invention is not limited to any particular kind of pressure sensor.

Pressure monitor 10 may also be coupled to an electrode 16 for sensing the electrical activity within heart 18. Pressure monitor 10 may estimate stroke volume or cardiac output as a function of the pressure signal, or both the pressure signal and the sensed electrical activity.

FIG. 1 also shows pressure monitor 10 coupled to an implantable medical device (IMD) 20, and communicating with a programmer 22. In some embodiments of the present invention, pressure monitor 10 may control the delivery of a therapy by IMD 20 as a function of the estimated stroke volume or cardiac output. Programmer 22 allows pressure monitor 10 to exchange information with a person, such as a physician or technician. The pressure monitor may output estimated stroke volumes or cardiac outputs to a physician or technician for analysis via programmer 22. The pressure monitor may output the stroke volumes or cardiac outputs in real-time, or the stroke volumes or cardiac outputs may be stored in memory for later retrieval.

Pressure sensor 14 and electrode 16 may, as shown in FIG. 1, be placed inside right ventricle 26 of heart 18. In other embodiments of the invention, pressure sensor 14 and electrode 16 may be placed inside left ventricle 30 of heart 18. The invention is not limited to either ventricle, but it is preferred that pressure sensor 14 be located within either the right ventricle 26 or the left ventricle 30, and be located proximate to either the pulmonary valve 34, as shown in FIG. 1, or the aortic valve 38. In the embodiment shown in FIG. 1, lead 12 extends from right ventricle 26, through right atrioventricular valve 32, and through superior vena cava 40. Lead 12 extends further through the patient's circulatory system, eventually exiting the circulatory system and coupling to pressure monitor 10.

Pressure monitor 10 and IMD 20 may, for example, be implanted in an abdomen or upper chest of a patient. Programmer 22 is located outside of the body of the patient, as indicated by dashed line 48.

Figure 2:
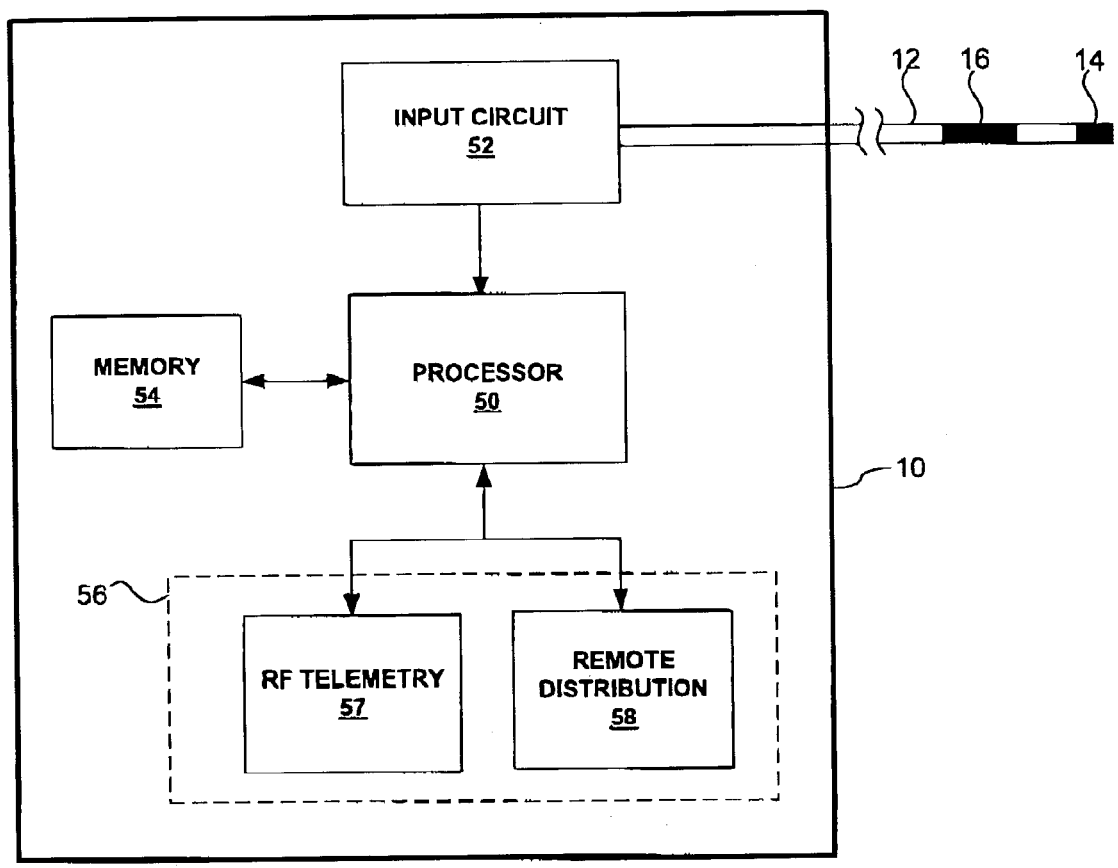
FIG. 2 is a block diagram illustrating one embodiment of the pressure monitor of the present invention.

FIG. 2 is a block diagram illustrating one embodiment of pressure monitor 10 of the present invention. Pressure monitor 10 includes an input circuit 52 that receives signals conducted along lead 12. These signals may include a pressure signal from pressure sensor 14, and a signal representative of the electrical activity within the heart sensed by electrode 16. Input circuit 52 may sample, demodulate or otherwise process the signals received via lead 12. Input circuit 52 delivers a pressure signal that is representative of the fluid pressure in heart 18 and an electrical activity signal that is representative of the electrical activity within heart 18 to a processor 50. Processor 50 estimates the stroke volume or cardiac output of the heart 18 as a function of the pressure signal, or both the pressure signal and the electrical activity signal received from input circuit 52.

Processor 50 may store data pertaining to the pressure in heart 18, and the estimated stroke volumes or cardiac outputs in memory 54. The data may reflect, for example, the pressure values, stroke volumes, or cardiac outputs, on a minute-to-minute basis, an hour-to-hour basis, or on some other basis.

This data may thereafter be retrieved via input/output circuitry 56, such as RF telemetry 57 and remote distribution link 58, via programmer 22. The data may be plotted for viewing by a physician or other clinician. Remote distribution link 58 provides a channel for downloading data from the patient over a telephone line or over the Internet, for example. RF telemetry 57 provides immediate access to the data on a dedicated channel. Typically, a patient is required to visit an office of the clinician when data are to be downloaded via RF telemetry 57.

Input/output circuitry 56 allows a user, such as the clinician, to exchange information with processor 50. The information exchanged may include pressure data, stroke volume data and cardiac output data, patient activity data, and other numbers, statistics or data. The information may also include programming parameters to direct the activity of processor 50 or other data that processor 50 may use when calculating stroke volume or cardiac output, both of which may be stored in memory 54.

Processor 50 may be implemented as an embedded microprocessor, controller, and the like, or as an ASIC, FPGA, discrete logic circuitry, or analog circuitry. Processor 50 may execute instructions stored in memory 54, which may comprise any computer-readable medium suitable for storing instructions including random access memory (RAM), read-only memory (ROM) non-volatile random access memory (NVRAM), electrically erasable programmable read-only memory (EEPROM), flash memory, and the like.

In general, the cardiac output (CO) is defined as the volume of blood pumped out of a ventricle the heart per minute. Cardiac output can be calculated as a function of the stroke volume (SV) and the heart rate as follows:

$$CO(\text{l/min}) = \frac{SV(\text{ml/beat}) \cdot HeartRate(\text{beats/min})}{1000 \ (\text{ml/l})} \quad (1)$$

The stroke volume is defined as the volume of blood pumped out of a ventricle of the heart per beat. As discussed above, one commonly used existing method for determining the stroke volume involves the use of echocardiography. Using echo-Doppler ultrasound equipment, the velocity of the blood as it travels through an outflow tract during a heartbeat may be measured. The outflow tract of interest may be pulmonary valve 34 or aortic valve 38.

In systole, right ventricle 26 and left ventricle 30 contract. For a brief period, no blood leaves right ventricles 26 and left ventricle 30, and the contraction is isovolumetric. During isovolumetric contraction, atrioventricular valves 32 and 36 are closed by backward pressure differential forces. Pulmonary valve 34 and aortic valve 38 are likewise closed, as the pressure in ventricles 26 and 30 is insufficient to force blood through them. Consequently, isovolumetric contraction causes the blood in ventricles 26 and 30 to undergo increasing pressure. In a short time, the pressure in right ventricle 26 overcomes the pressure in pulmonary arteries 42 and 44, drives pulmonary valve 34 open, and ejects blood from right ventricle 24 into pulmonary arteries 42 and 44. Similarly, the pressure in left ventricle 30 overcomes the pressure in aorta 46, driving open aortic valve 38 and ejecting blood into aorta 46. The pressure needed to open aortic valve 38 is normally much higher than the pressure needed to open pulmonary valve 34.

Considering the right ventricle 26, for example, when the pulmonary valve 34 is closed no blood flows through it, thus the velocity of blood flowing through pulmonary valve 34 is zero. At the time of valve opening the velocity of the blood flowing through pulmonary valve 34 may also be assumed to be zero. With the valve open, however, the velocity of the blood begins increasing to a peak velocity due to a pressure gradient across the valve caused by the contraction of the right ventricle 26. The velocity then decreases from the peak velocity due to the diminishing pressure gradient until the pressure in right ventricle 26 is once again equal to the pressure in the pulmonary arteries 42 and 44. At that time, the valve closes and the velocity of blood flowing through the valve is once again zero.

Conventional echocardiography periodically measures the velocity of the blood flowing through an outflow tract during a beat. These measurements are used to form a curve that is representative of the change in velocity during the beat, which is sometimes referred to as the velocity-time function. Integrating the curve between the valve opening and the valve closing yields what is known as the velocity-time integral (VTI). The velocity-time integral is a linear measurement of the amount of blood that has flown through the outflow tract. To determine the stroke volume, the cross-sectional area (CSA) of the outflow tract must also be determined.

$$SV(\text{ml/beat}) = CSA(\text{cm}^2) \cdot VTI(\text{cm/beat}) \quad (2)$$

Using echo-Doppler ultrasound, the outflow tract diameter (OTD) may be measured. Assuming that the pulmonary valve 34 is a circle, stroke volume may be determined according to the following equation:

$$SV(\text{ml/beat}) = \pi \cdot \left(\frac{OTD(\text{cm})}{2}\right)^2 \cdot VTI(\text{cm/beat}) \quad (3)$$

Processor 50 may use equation (3) to determine stroke volume, or equation (3) and equation (1) to determine cardiac output. Unlike conventional techniques that make use of velocity data to directly calculate the velocity-time integral, as is done via echocardiography, processor 50 estimates the velocity-time function or the velocity-time integral as a function of the pressure signal received from lead 12.

As will be described in greater detail below, processor 50 estimates the velocity-time function or the velocity-time integral by calculating a peak pressure gradient by making use of a simplified Bernoulli equation as follows:

$$\Delta p_{peak} = 4V_2^2 \quad (4)$$

where: $\Delta p_{peak}$ is the peak pressure gradient, and $V_2$ is the peak velocity Considering right ventricle 26, the peak pressure gradient across the pulmonary valve 26 is the difference between the peak pressure within right ventricle 26, on one side of pulmonary valve 34, and the lowest pressure within the pulmonary arteries 42 and 44 while pulmonary valve 34 is open, on the other side of pulmonary valve 34.

Figure 3:
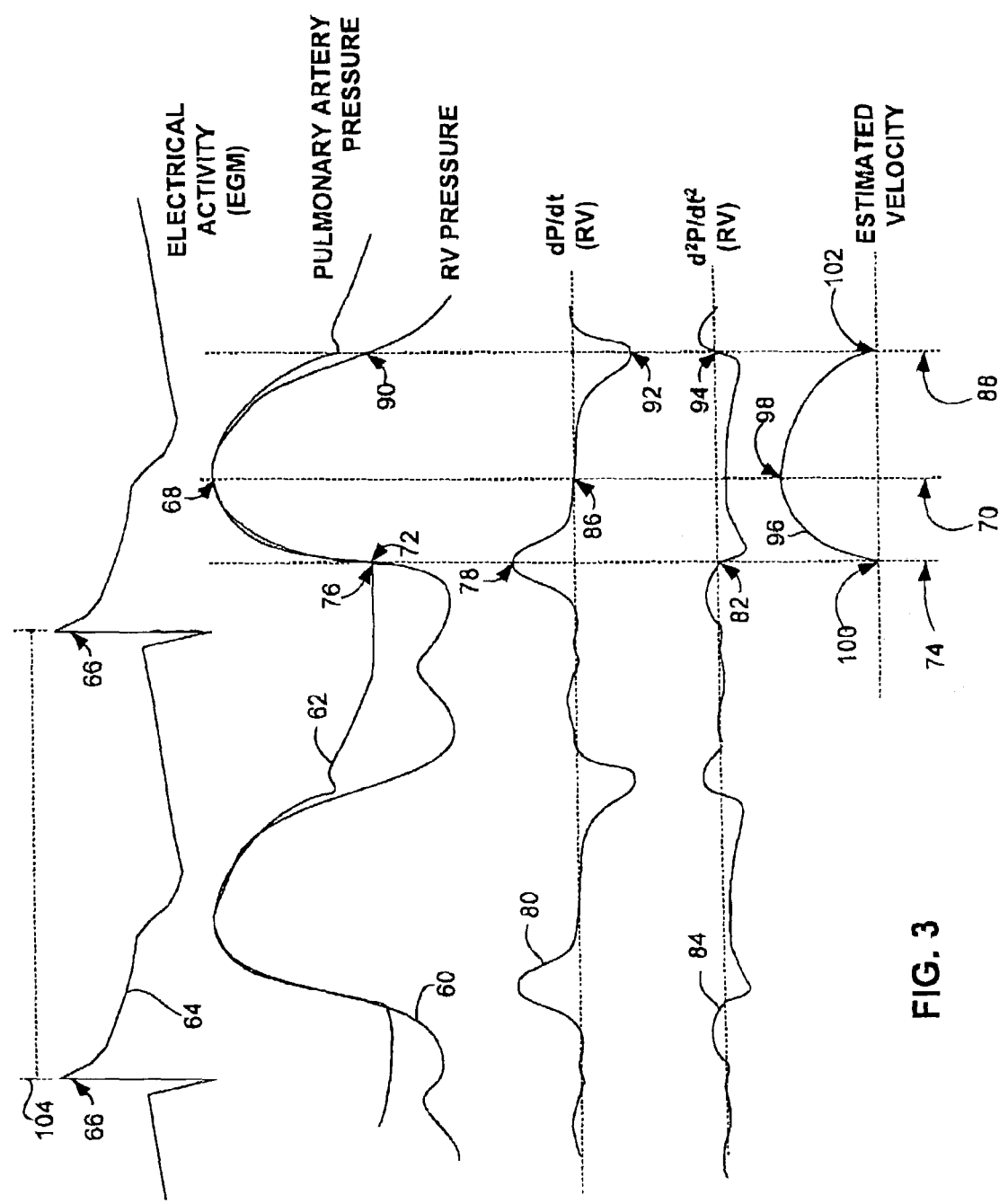
FIG. 3 is a timing diagram providing an overview of an exemplary mode of operation of the pressure monitor to estimate a rate of blood flow from the heart according to the invention.

FIG. 3 is a timing diagram providing an overview of an exemplary mode of operation of the pressure monitor 10 to estimate a rate of blood flow from heart 18 according to the invention. In particular, the timing diagram is useful to illustrate the techniques employed by processor 50 to identify the peak pressure within the right ventricle 26 and the pressure within the pulmonary arteries 42 and 44 at the time when pulmonary valve 34 opens. Right ventricular pressure signal 60 represents a signal produced by pressure sensor 14 indicative of the fluid pressure in right ventricle 26 of heart 18. For exemplary purposes, the right ventricular pressure signal is shown superimposed on a graph 62 illustrating the fluid pressure within pulmonary arteries 42 and 44. Right ventricular pressure signal 60 is also shown in reference to right ventricular EGM 64 that represents the electrical activity within heart 18 as sensed by electrode 16 from within right ventricle 26.

Processor 50 receives a pressure signal 60 representative of right ventricular pressure from pressure sensor 14 located in right ventricle 26 via input circuit 52 as described above. Input circuit 52 senses the electrical activity within heart 18 via electrode 16, and delivers an electrical activity signal representative of right ventricular EGM 64 to processor 50 as described above.

R-wave 66 in EGM signal 64 of FIG. 3 represents ventricular depolarization of heart 18. Following ventricular depolarization, pressure in right ventricle 26 increases, eventually reaching a peak pressure at 68. Peak pressure 68 is often referred to as the right ventricular systolic pressure, or RVSP. In order to calculate the pressure gradient across the pulmonary valve 34, processor 50 identifies the RVSP 68. Processor 50 may identify RVSP 68 by, for example, applying a peak detection algorithm to the pressure signal representative of right ventricular pressure signal 60 that processor 50 receives from input circuit 52. Peak detection algorithms are well known in the art. Processor 50 may also identify the time at which the peak pressure occurs, which is identified on FIG. 3 by line 70, for reasons that will be discussed below.

In order to calculate the pressure gradient across pulmonary valve 34, processor 50 must also identify the lowest pressure within pulmonary arteries 42 and 44 while pulmonary valve 34 is open. This pressure is approximately the lowest pressure within pulmonary arteries 42 and 44 during a cardiac cycle, which is referred to as the pulmonary artery diastolic pressure, or PAD. This pressure occurs at the time of valve opening, which is identified on FIG. 3 by line 74, and is identified on pulmonary artery pressure signal 62 at 72. Because pressure sensor 14 is not located within the pulmonary arteries 42 and 44, processor 50 cannot directly identify pressure 72.

Processor 50 identifies pressure 72 indirectly by identifying the pressure 76 of right ventricular pressure signal 60 at the time of valve opening 74. During isovolumetric contraction in systole, the pressure in right ventricle 26 increases and forces pulmonary valve 34 open. Prior to the time of valve opening 74, the pressure within right ventricle 26 is less than the pressure in pulmonary arteries 42 and 44 as illustrated by right ventricular pressure signal 60 and pulmonary artery pressure signal 62 of FIG. 3. The greater pressure in the pulmonary arteries 42 and 44 keeps pulmonary valve 34 closed. As illustrated by right ventricular pressure signal 60 and pulmonary artery pressure signal 62, the pressure within right ventricle 26 increases until it is equal to the pressure within pulmonary arteries 42 and 44, at which point the pulmonary valve 34 is forced open. Therefore, at the time of valve opening 74, the pressure within right ventricle 26 is equal to pressure 72. The pressure within right ventricle 26 at the time of valve opening 74 is often referred to as the estimated pulmonary artery diastolic pressure, or ePAD.

Processor 50 identifies ePAD 76 by processing the pressure signal that it receives from input circuit 52 to identify the time of valve opening 74. As described above, when the pressure in right ventricle 26 overcomes the pressure in pulmonary arteries 42 and 44, pulmonary valve 34 is driven open. When pulmonary valve 34 opens, contraction is no longer isovolumetric. Pressure in right ventricle 26, although still increasing due to ventricular contraction, increases at a slower rate. As a result, there is an inflection point in right ventricular pressure signal 60 at the time of valve opening 74. It is this change in the rate of increase of right ventricular pressure, or inflection point, that allows processor 50 to identify the time of valve opening 74 and ePAD 76.

The inflection point of right ventricular pressure signal 60 may be identified by taking the first derivative of right ventricular pressure with respect to time, or dP/dt. Because the slope of right ventricular pressure signal 60 is at its maximum positive value at the inflection point, the positive peak 78 of dP/dt signal 80 corresponds to the inflection point. Therefore, ePAD 76 may be found by finding the point on right ventricular pressure signal 60 corresponding to the maximum positive value of dP/dt signal 80. The inflection point may also be found by taking the second derivative of right ventricular pressure with respect to time, or $d^2P/dt^2$. In this case, ePAD 76 is the pressure at the point on right ventricular pressure signal 60 corresponding to the point 82 at which signal 84 of $d^2P/dt^2$ goes negative for the first time after R-wave 66. As illustrated in FIG. 3, both the peak 78 of dP/dt signal 80 and the zero-crossing 82 of $d^2P/dt^2$ signal 84 occur at the time of valve opening 74. Processor 50 may differentiate the pressure signal that it receives from input circuit 52 to determine the first or second derivative of the pressure signal with respect to time. Processor 50 may further apply algorithms to detect when the first derivative of the pressure signal peaks, or to identify the occurrence of R-wave 66 in the electrical activity signal received from input circuit 52 and identify when the second derivative becomes negative after the R-wave 66. By detecting when the inflection point occurs, processor 50 may identify the pressure in right ventricle 26 at the inflection point, which is ePAD 76, and the time of valve opening 74.

In addition to the method for identifying RVSP 68 and the time of peak pressure 70 described above, processor 50 may also identify RVSP 68 and the time of peak pressure 70 by determining the first derivative of the pressure signal received from input circuit 52. As illustrated by FIG. 3, at its peak, the slope of right ventricular pressure signal 60 goes from positive to negative. Thus, RVSP 68 and time of peak pressure 70 occur at the point 86 when dP/dt signal 80 goes negative for the first time after R-wave 66. Processor 50 may identify RVSP 68 and time of peak pressure 70 by identifying the occurrence of R-wave 66 in the electrical activity signal received from input circuit 52 and when the first derivative becomes negative after the R-wave 66.

Processor 50 may also identify the time of valve closing 88 by determining the first or second derivative of the pressure signal. As illustrated by right ventricular pressure signal 60 in FIG. 3, after RSVP 68 the pressure in right ventricle 26 begins to decrease due to the continued ejection of blood from right ventricle 26 into to pulmonary arteries 42 and 44. When pulmonary valve 34 closes at time of valve closing 88, the pressure in right ventricle 26 continues to decrease due to relaxation of right ventricle 26. This continued decrease in pressure, however, occurs at a slower rate. Thus, there is another inflection point 90 in right ventricular pressure signal 60 at the time of valve closing 88.

Because the slope of right ventricular pressure signal 60 is at its maximum negative value at inflection point 90, the most negative point 92 of dP/dt signal 80 corresponds to inflection point 90. Therefore, the time of valve closing 88 may be identified by identifying the time corresponding to the most negative point 92 of dP/dt signal 80. Time of valve closing 88 may also be identified by identifying the time corresponding to the point 94 at which signal 84 of $d^2P/dt^2$ goes positive for the first time after R-wave 66. As illustrated in FIG. 3, both the most negative point 92 of dP/dt signal 80 and the zero-crossing 94 of $d^2P/dt^2$ signal 84 occur at the time of valve closing 88.

In order to identify when inflection point 90 occurs, processor 50 may apply algorithms to detect when the most negative value of the first derivative of the pressure signal occurs, or to identify the occurrence of R-wave 66 in the electrical activity signal received from input circuit 52 and identify when the second derivative becomes positive after the R-wave 66. By detecting when the inflection point 90 occurs, processor 50 may identify the time of valve closing 88.

Having identified RVSP 68 and ePAD 76, processor 50 may calculate the peak pressure gradient as the difference between RVSP 68 and ePAD 76.

$$\Delta p_{peak} = RVSP - ePAD \tag{5}$$

Having calculated the peak pressure gradient, processor 50 may estimate the peak velocity of the blood flowing through pulmonary valve 34 by solving the simplified Bernoulli equation (4) for the peak velocity and substituting the calculated pressure difference for the pressure gradient.

$$V_2 = \sqrt{\frac{\Delta p_{peak}}{4}} \tag{6}$$

$$V_2 = \frac{1}{2}\sqrt{(RVSP - ePAD)} \tag{7}$$

In some embodiments of the invention, processor 50 may estimate a velocity-time function, such as the estimated velocity-time function illustrated by signal 96 shown in FIG. 3, using the estimated peak velocity 98, the time of valve opening 74, time of peak pressure 70 and time of valve closing 88. As discussed above, prior to the time of valve opening and after the valve has closed, when pulmonary valve 34 is closed, the velocity of blood flowing through pulmonary valve 34 is zero. Therefore, the velocity of blood flowing through pulmonary valve 34 at the time of valve opening 74 and the time of valve closing 88 may be assumed to be zero as shown on estimated velocity-time signal 96 at point 100 and point 102. Further, it can be assumed that the peak velocity 98 of blood flowing through pulmonary valve 34 occurs at the time of peak pressure 70 within right ventricle 26. The two segments of the estimated velocity-time function represented by signal 96, from the time of valve opening 74 to the time of peak pressure 70 and from the time of peak pressure 70 to the time of valve closing 88, are assumed to be parabolas. The use of this assumption is supported by reference to actual velocity-time signals measured by echocardiography, which are parabolic in shape. The following estimated velocity-time function describes signal 96:

$t = t_1 =$ time of valve opening 74: $V=0$ \quad (8)

$t = t_2 =$ time of peak pressure 70: $V = V_2$ $t = t_3 =$ time of valve closing 88: $V = 0$ $$t_1 < t < t_2: \quad v = \frac{-V_2}{\Delta t_1^2} \cdot t^2 + \frac{2V_2}{\Delta t_1} \cdot t$$

$$t_2 < t < t_3: \quad v = \frac{-V_2}{\Delta t_2^2} \cdot (t + \Delta t_2 - \Delta t_1)^2 + \frac{2V_2}{\Delta t_2} \cdot (t + \Delta t_2 - \Delta t_1)$$

Figure 4:
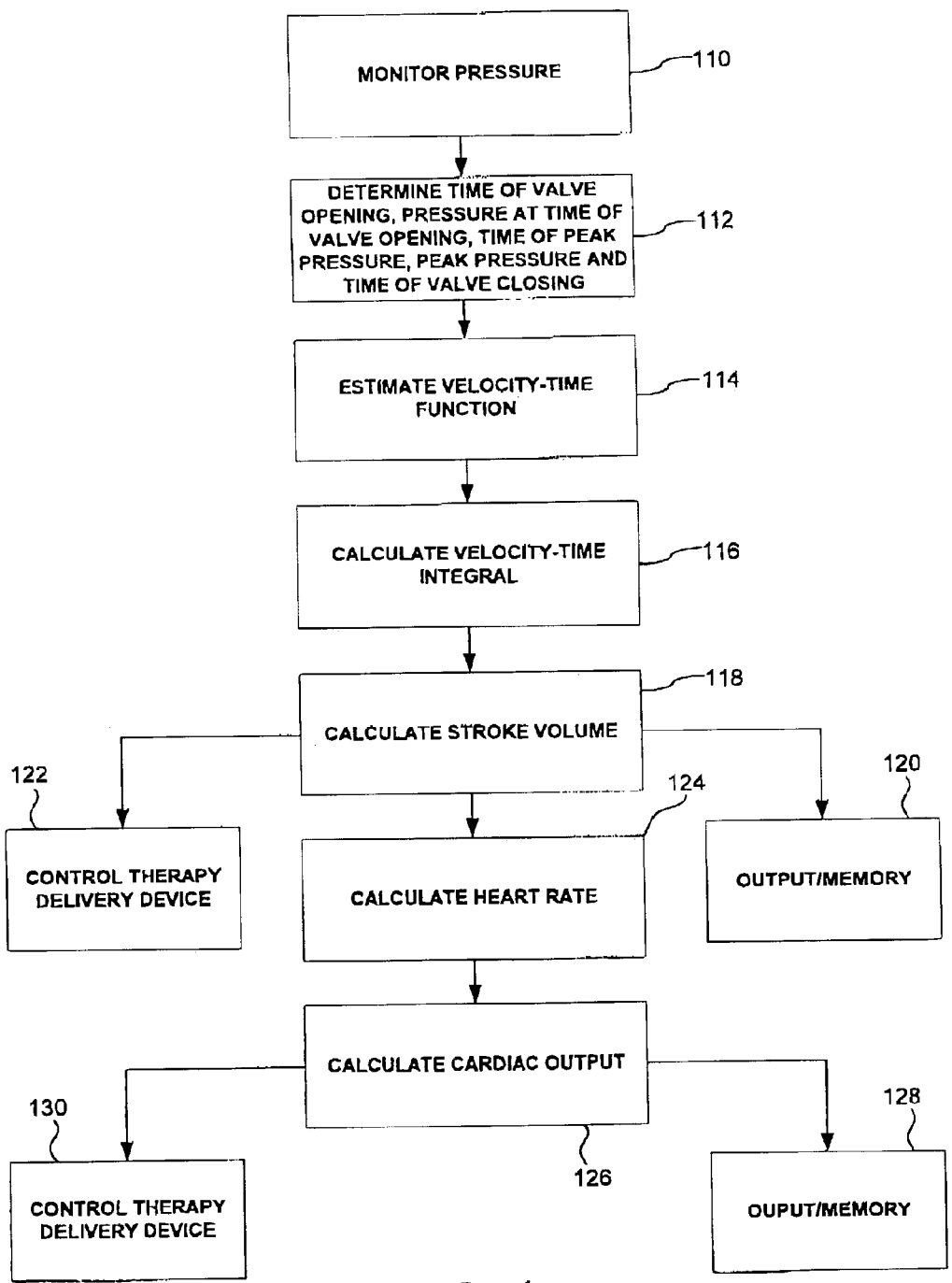
FIG. 4 is a flow diagram further illustrating the operation of the pressure monitor according to the invention.

FIG. 4 is a flow diagram further illustrating the operation of pressure monitor 10 according to the invention. Pressure monitor 10 monitors a pressure within heart 18, a pressure within right ventricle 26 for example (110). Pressure sensor 14 may sense the pressure in right ventricle 26, and generate a signal representative of the sensed pressure. Pressure monitor 10 may receive the signal generated by pressure sensor 14 and conducted along lead 12 via input circuit 52. Input circuit 52 may sample, demodulate or otherwise process the signal. Input circuit 52 may deliver a pressure signal representative of the pressure sensed within the right ventricle 26 to processor 50 of pressure monitor 10.

Processor 50 may analyze the pressure signal to determine the time of valve opening 74, the pressure at the time of valve opening, or ePAD 76, the time of peak pressure 70, the peak pressure, or RVSP 68, and the time of valve closing 88 (112). Processor 50 may then use these values to estimate a velocity-time function (114). Processor 50 may determine the values and estimate the velocity time function by any of the methods described above.

Processor 50 may calculate the velocity time integral as a function of the estimated velocity-time function (116). In some embodiments of the present invention, processor 50 may integrate the estimated velocity-time function (8), or the signal 96 that equation (8) describes. In either case, the result of the integration by processor 50 is an estimated velocity-time integral.

Processor 50 may use the estimated velocity-time integral to calculate the stroke volume by applying equation (3) (118). The outflow tract diameter, or OTD, may be measured once by echocardiography, and used as a constant for the particular patient in whom pressure monitor 10 is implanted. This OTD value may be received from programmer 22 via input/output circuitry 56, and stored in memory 54. The OTD value for a patient will vary little over time, but the value could, of course, be updated at subsequent office visits.

The stroke volume calculated by processor 50 may then be output to a physician via output circuitry 56 and programmer 22, or stored in memory 54 for later retrieval as described above (120). In some embodiments of the invention, processor 50 may also, as will be described in more detail below, control the delivery of therapy by an implantable medical device as a function of the calculated stroke volume (122).

Processor 50 may calculate the heart rate (124) by analyzing an electrical activity signal received from input circuit 52. As described above, the electrical activity signal is representative of the electrical activity sensed within heart 18 by input circuit 52. Input circuit 52 senses the electrical activity within heart 18 via electrode 16 located in right ventricle 26, which is coupled to input circuit 52 by lead 12. Processor 50 may calculate the heart rate by identifying the occurrence of R-waves 66 of the electrical activity signal. Processor 50 may also calculate the beat-to-beat heart rate by measuring an R—R interval 104, which is the time between the occurrences of R-waves 66 as shown in FIG. 3.

$$HeartRate(\text{beats/min})_{beat-to-beat} = \frac{60(\text{s/min})}{t_{R-R} \ (\text{s/beat})} \tag{9}$$

Processor 50 may use the calculated stroke volume and heart rate to calculate the cardiac output (126) by applying equation (1). In embodiments of the invention where stroke volume is calculated on a beat-to-beat basis, processor 50 may calculate cardiac output using the following beat-to-beat cardiac output equation derived by substituting the beat-to-beat heart rate of equation (9) into the cardiac output equation (1).

$$CO(\text{l/min}) = \frac{60(\text{s/min})}{t_{R-R} \ (\text{s/beat})} \cdot \frac{SV(\text{ml/beat})}{1000(\text{ml/l})} \tag{10}$$

The calculated cardiac output may also be output via input/output circuitry 56 or stored in memory 54 (128), as was described above with respect to the stroke volume.

Processor 50 may also, as will be described in more detail below, control the delivery of therapy by an implantable medical device as a function of the calculated cardiac output (130).

The techniques of the invention described with reference to FIG. 4 involve estimation and integration of a velocity-time function by processor 50, in order to determine an estimated velocity-time integral that can be used to calculate the stroke volume and cardiac output. Integration of the estimated velocity-time function (8), however, leads to another embodiment of the invention. This embodiment does not require estimation or integration of a velocity-time function in order to calculate an estimated velocity-time integral. The integration of velocity-time function (8) to determine the velocity-time integral (VTI) simplifies as follows:

$$VTI = \int_0^{\Delta t_1}\left(\frac{-V_2}{\Delta t_1^2}\cdot t^2 + \frac{2V_2}{\Delta t_1}\cdot t\right)dt + \int_0^{\Delta t_2}\left(\frac{-V_2}{\Delta t_2^2}\cdot t^2 + \frac{2V_2}{\Delta t_2}\cdot t\right)dt \quad (11)$$

$$VTI = \left(\frac{-V_2}{3\Delta t_1^2}\cdot t^3 + \frac{V_2}{\Delta t_1}\cdot t^2\right)\bigg|_0^{\Delta t_1} + \left(\frac{-V_2}{3\Delta t_2^2}\cdot t^3 + \frac{V_2}{\Delta t_2}\cdot t^2\right)\bigg|_0^{\Delta t_2} \quad (12)$$

$$VTI = \left(\frac{-V_2}{3\Delta t_1^2}\cdot \Delta t_1^3 + \frac{V_2}{\Delta t_1}\cdot \Delta t_1^2\right) + \left(\frac{-V_2}{3\Delta t_2^2}\cdot \Delta t_2^3 + \frac{V_2}{\Delta t_2}\cdot \Delta t_2^2\right) \quad (13)$$

$$VTI = \frac{2}{3}\cdot V_2 \cdot (\Delta t_1 + \Delta t_2) \quad (14)$$

where: $(\Delta t_1 + \Delta t_2) = (t_2 - t_1 + t_3 - t_2) = (t_3 - t_1)$

Combining equations (7) and (14) yields an equation that allows the calculation of an estimated velocity-time integral value directly from pressure and time values determined by processor 50.

$$VTI = \frac{1}{3}\cdot \sqrt{(RVSP - ePAD)}\cdot (t_3 - t_1) \quad (15)$$

Figure 5:
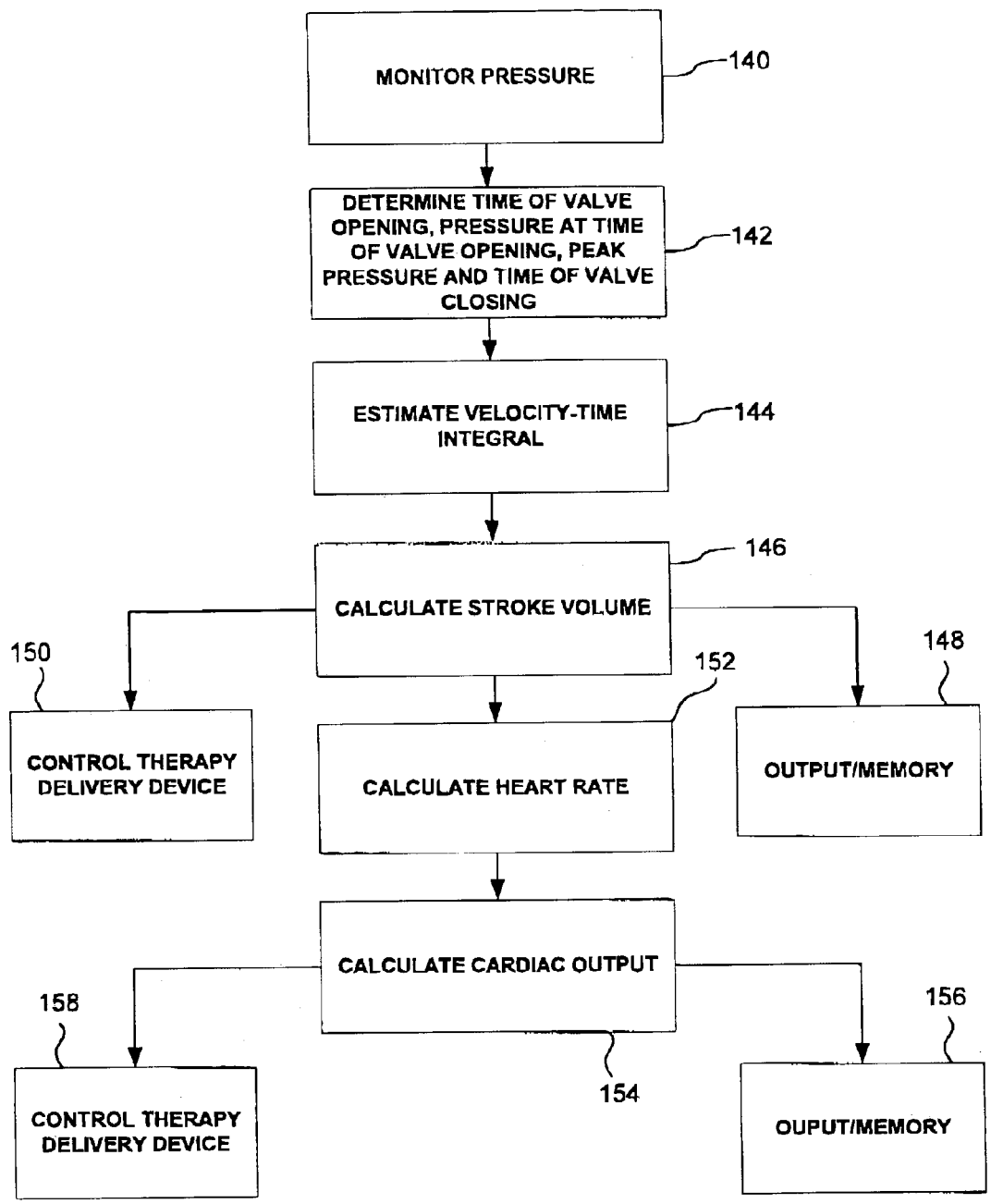
FIG. 5 is a flow diagram illustrating one mode of operation of the pressure monitor according to the invention.

Techniques for pressure-based estimation of stroke volume and cardiac output that do not involve estimation or integration of a velocity-time function are shown in FIG. 5. Pressure monitor 10 monitors a pressure within right ventricle 26 as described above with respect to FIG. 4 (140). In the embodiment described by FIG. 5, processor 50 may analyze the pressure signal to determine the time of valve opening 74, the pressure at the time of valve opening, or ePAD 76, the peak pressure, or RVSP 68, and the time of valve closing 88 (142). In this embodiment, processor 50 need not determine the time of peak pressure 70. Processor 50 may then use these pressure and time values to estimate a velocity-time integral value (144). Processor 50 may determine the pressure and time values by any of the methods described above. Processor 50 may, as described above with respect to FIG. 4, calculate a stroke volume (146) using this value of VTI, and calculate a cardiac output (154) as a function of a calculated heart rate (152) and the stroke volume. Further, the stroke volume or cardiac output calculated by processor 50 may be output to a physician via output circuitry 56 and programmer 22 or stored in memory 54 for later retrieval (148 or 156), or may be used to control the delivery of therapy by an implantable medical device as a function of the calculated stroke volume or cardiac output (150 or 158).

Processor 50 may determine pressures and times, and estimate stroke volume or cardiac output as often as on a beat-to-beat basis. However, the present invention is not limited to making these determinations and estimations on any particular basis. The determinations and estimations may be made on a minute-to-minute basis, hour-to-hour basis, or on any basis. The determinations and estimations could also be made in response to a signal from a physician or patient.

As mentioned above, it is preferred that pressure sensor 14 be placed proximate to either pulmonary valve 34, as shown in FIG. 1, or aortic valve 36. That is because the present invention makes use of equations derived from the simplified Bernoulli equation (4), which describes the relationship between the peak velocity of blood flowing through a heart valve and the pressure gradient. The use of these equations assumes that the pressure gradient is measured in the outflow tract, as close as possible to the heart valve. If pressure sensor 14 is located elsewhere in the ventricle, the estimated peak velocity or the estimated velocity-time integral value will be lower than the actual peak velocity or actual velocity-time integral because the area through which the blood volume flows is larger.

In order to make the estimation of stroke volume or cardiac output as independent of the location of pressure sensor 14 and other potential sources or error as possible, it may be desirable to compare a result of the implantable system with the result of another stroke volume or cardiac output measurement technique to obtain a correction constant. The correction constant may then be, for example, transmitted to pressure monitor 10 via programmer 22 and input/output circuits 56, where it can be stored in memory 54 for later use by processor 50 in its estimation of stroke volume or cardiac output.

Figure 6:
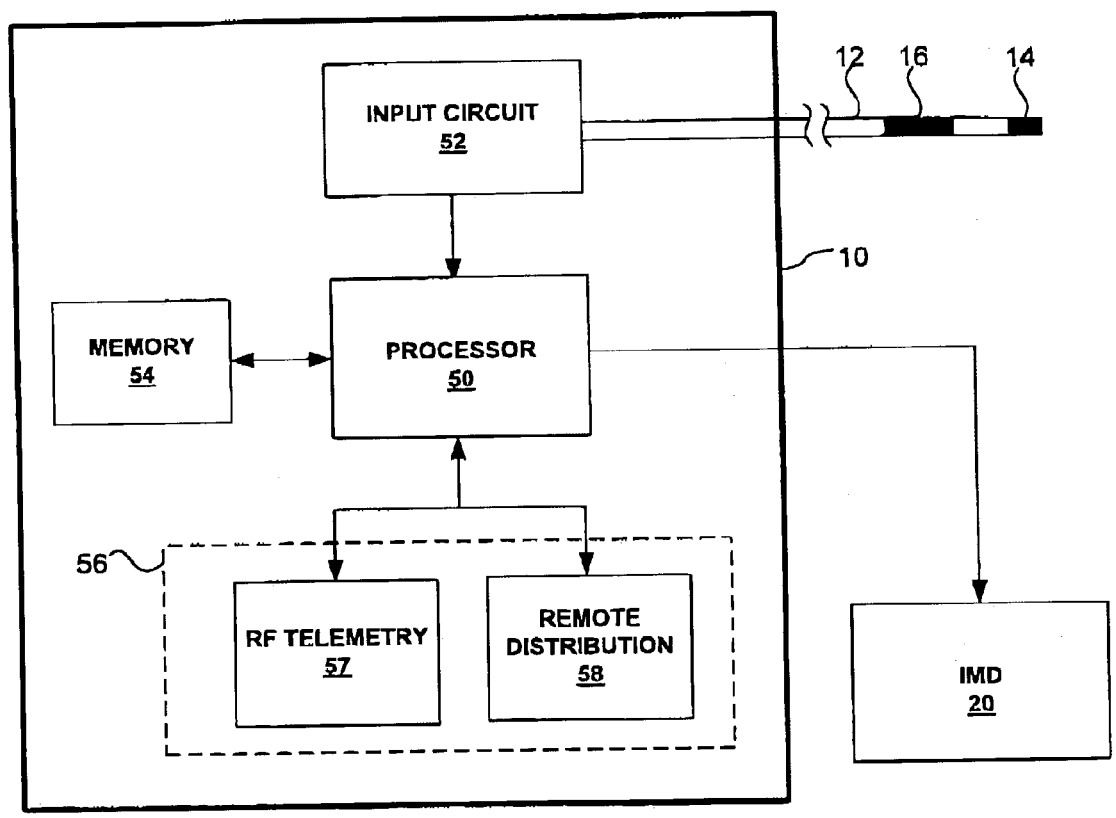
FIG. 6 is a block diagram of an exemplary embodiment of the pressure monitor of the present invention shown in relation to an implantable medical device.

As mentioned above, in some embodiments of the invention processor 50 of pressure monitor 10 may control the delivery of a therapy by an implantable medical device, or IMD 20. FIG. 6 shows that processor 50 of pressure monitor 10 may generate a control signal as a function of the estimated stroke volume or cardiac output. Processor 50 delivers this control signal to IMD 20 to control the operation of IMD 20. In FIG. 1, the pressure monitor 10 and IMD 20 are shown coupled together. In such an embodiment, processor 50 may, for example, deliver the control signal to IMD 20 via a bus or data link. Alternatively, processor 50 may communicate with IMD 20 via input/output circuit 56, in a similar manner to its method of communication with programmer 22. Pressure monitor 10 and IMD 20 may or may not be physically coupled, may or may not be implanted near each other, and may or may not form a single implantable device.

Figure 7:
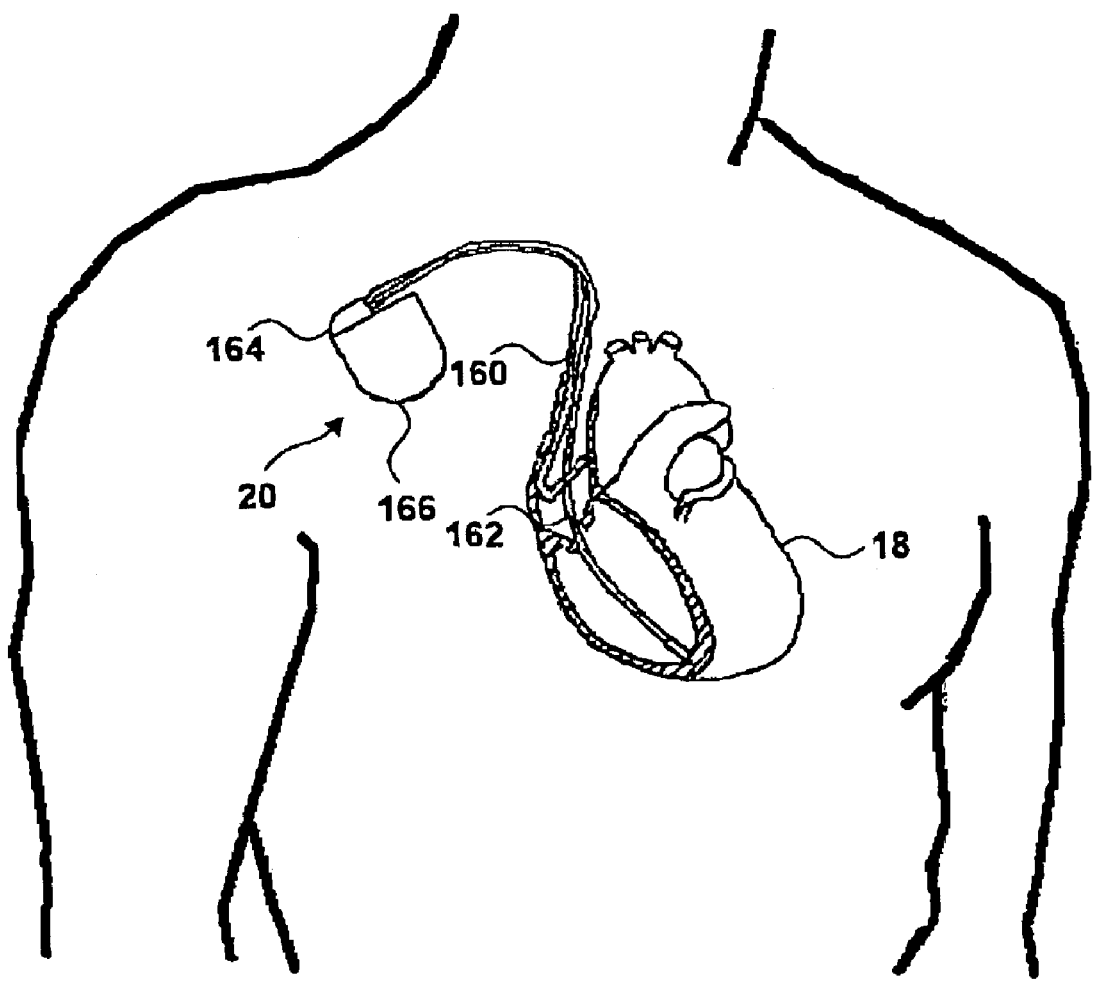
FIG. 7 is a schematic view of an exemplary implantable medical device.

FIG. 7 is a simplified schematic view of one embodiment of IMD 20 of the present invention. IMD 20 shown in FIG. 7 is a pacemaker comprising at least one of pacing and sensing leads 160 and 162 attached to connector module 164 of hermetically sealed enclosure 166 and implanted near human or mammalian heart 18. Pacing and sensing leads 160 and 162 sense electrical signals attendant to the depolarization and repolarization of the heart 18, and further provide pacing pulses for causing depolarization of cardiac tissue in the vicinity of the distal ends thereof. Leads 160 and 162 may have unipolar or bipolar electrodes disposed thereon, as is well known in the art. Examples of IMD 20 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 8:
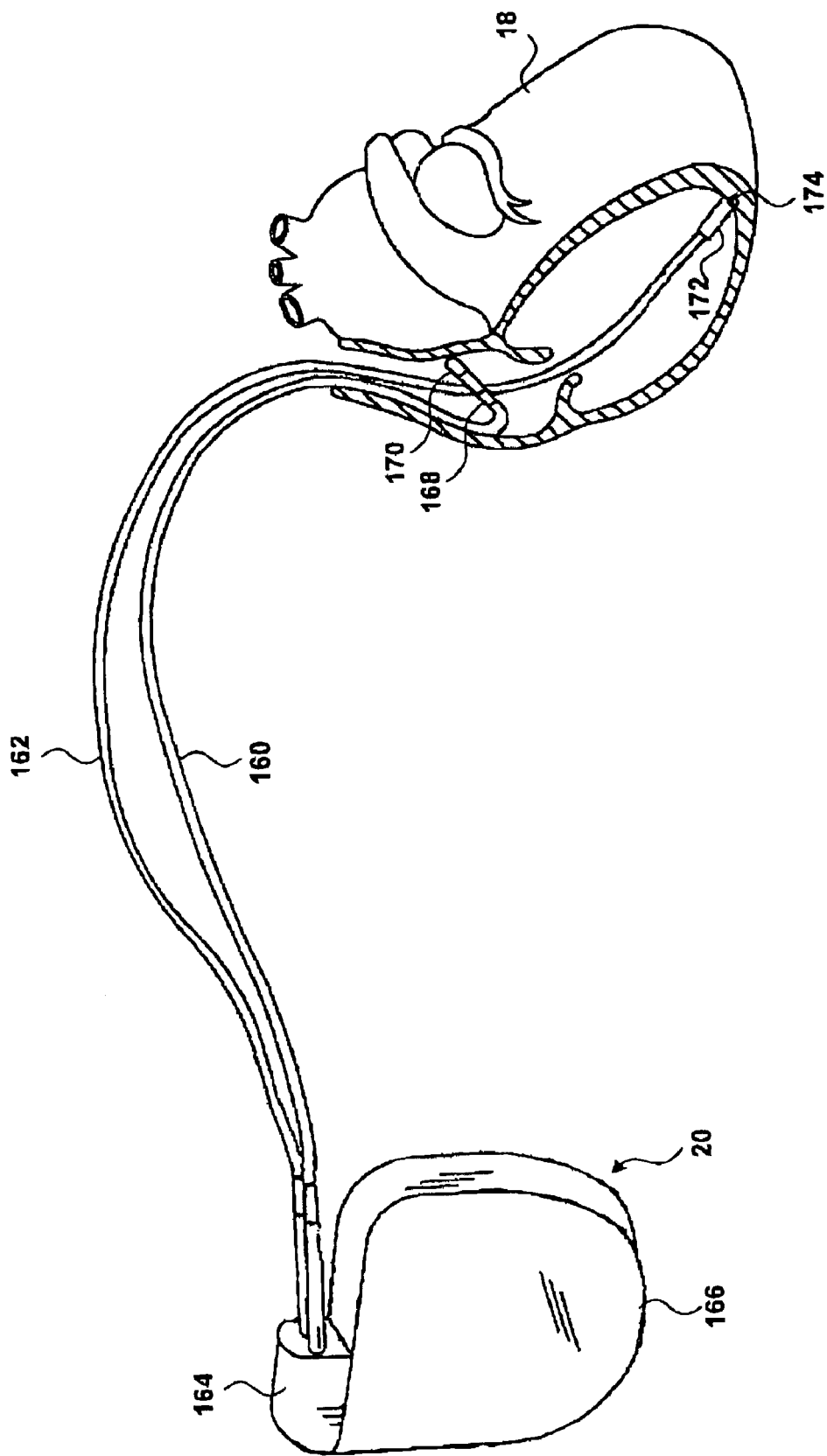
FIG. 8 shows the implantable medical device located in and near a heart.

FIG. 8 shows connector module 164 and hermetically sealed enclosure 166 of IMD 20 located in and near human or mammalian heart 18. Atrial and ventricular pacing leads 160 and 162 extend from connector module 164 to the right atrium and ventricle, respectively, of heart 18. Atrial electrodes 168 and 170 disposed at the distal end of atrial pacing lead 160 are located in the right atrium. Ventricular electrodes 172 and 174 disposed at the distal end of ventricular pacing lead 162 are located in the right ventricle.

Figure 9:
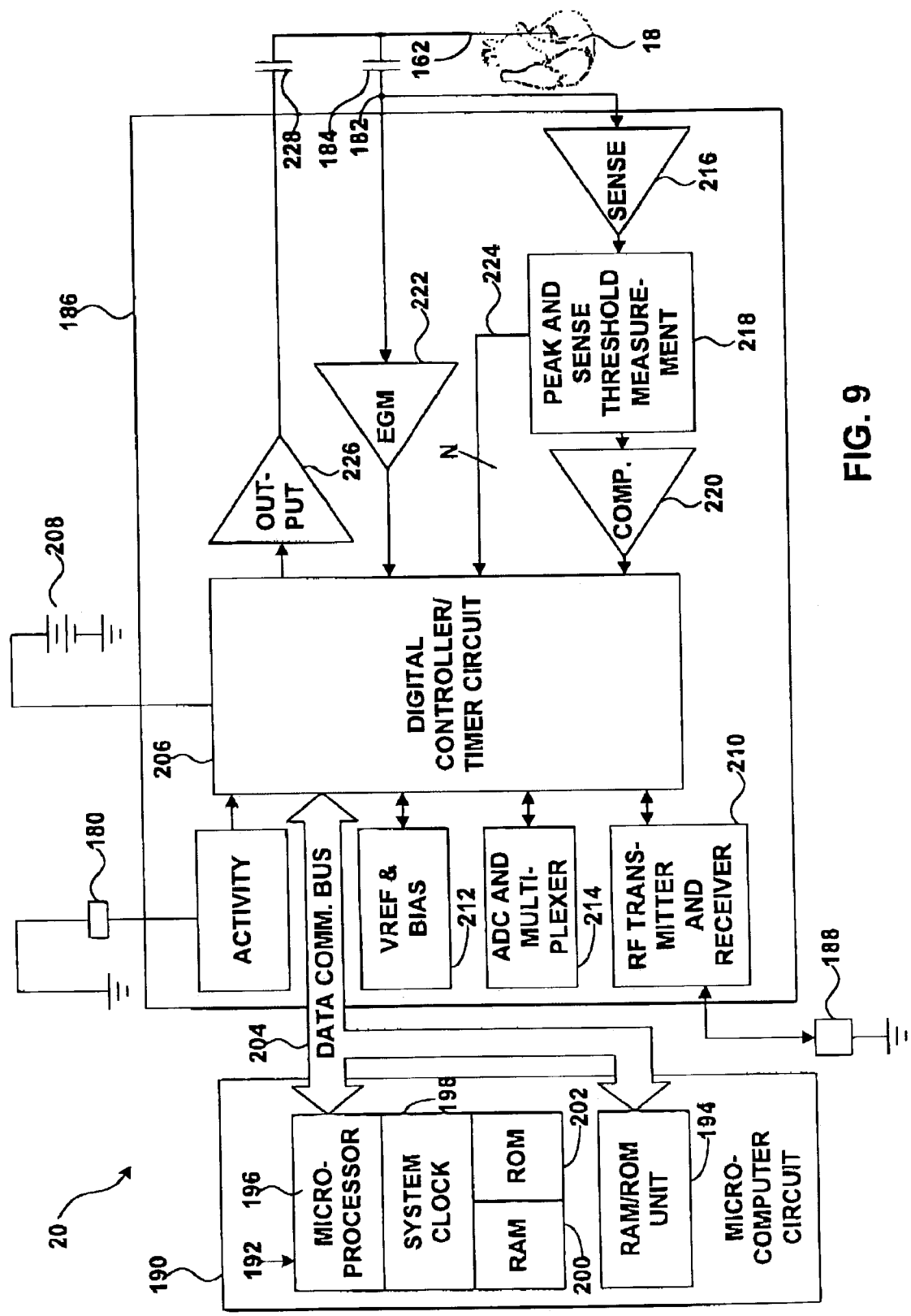
FIG. 9 is a block diagram illustrating the constituent components of an implantable medical device.

FIG. 9 shows a block diagram illustrating the constituent components of IMD 20 in accordance with one embodiment of the present invention, where IMD 20 is a pacemaker having a microprocessor-based architecture. IMD 20 is shown as including activity sensor or accelerometer 180, which is preferably a piezoceramic accelerometer bonded to a hybrid circuit located inside enclosure 166 (shown in FIGS. 7 and 8). Activity sensor 180 typically (although not necessarily) provides a sensor output that varies as a function of a measured parameter relating to a patient's metabolic requirements. For the sake of convenience, IMD 20 in FIG. 9 is shown with lead 162 only connected thereto. However, it is understood that similar circuitry and connections not explicitly shown in FIG. 9 apply to lead 160 (shown in FIGS. 7 and 8).

IMD 20 in FIG. 9 is most preferably programmable by means of an external programming unit, such as programmer 22 of FIG. 1. One such programmer is the commercially available Medtronic Model 9790 programmer, which is microprocessor-based and provides a series of encoded signals to IMD 20, typically through a programming head which transmits or telemeters radio-frequency (RF) encoded signals to IMD 20. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 9, lead 162 is coupled to node 182 in IMD 20 through input capacitor 184. Activity sensor or accelerometer 180 is most preferably attached to a hybrid circuit located inside hermetically sealed enclosure 166 of IMD 20. The output signal provided by activity sensor 180 is coupled to input/output circuit 186. Input/output circuit 186 contains analog circuits for interfacing with heart 18, activity sensor 180, antenna 188 and circuits for the application of stimulating pulses to heart 18. The rate of heart 18 is controlled by software-implemented algorithms stored within microcomputer circuit 190.

Microcomputer circuit 190 preferably comprises on-board circuit 192 and off-board circuit 194. Circuit 190 may correspond to a microcomputer circuit disclosed in U.S. Pat. No. 5,312,453 to Shelton et al., hereby incorporated by reference herein in its entirety. On-board circuit 192 preferably includes microprocessor 196, system clock circuit 198 and on-board RAM 200 and ROM 202. Off-board circuit 194 preferably comprises a RAM/ROM unit. On-board circuit 192 and off-board circuit 194 are each coupled by data communication bus 204 to digital controller/timer circuit 206. Microcomputer circuit 190 may comprise a custom integrated circuit device augmented by standard RAM/ROM components.

Electrical components shown in FIG. 9 are powered by an appropriate implantable battery power source 208 in accordance with common practice in the art. For the sake of clarity, the coupling of battery power to the various components of IMD 20 is not shown in the Figures.

Antenna 188 is connected to input/output circuit 186 to permit uplink/downlink telemetry through RF transmitter and receiver telemetry unit 210. By way of example, telemetry unit 210 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 188, input/output circuit 186 and telemetry unit 210 presented herein are shown for illustrative purposes only, and are not intended to limit the scope of the present invention.

Continuing to refer to FIG. 9, VREF and bias circuit 212 most preferably generates stable voltage reference and bias currents for analog circuits included in input/output circuit 186. Analog-to-digital converter (ADC) and multiplexer unit 214 digitizes analog signals and voltages to provide "real-time" telemetry intracardiac signals and battery end-of-life (EOL) replacement functions. Operating commands for controlling the timing of IMD 20 are coupled from microprocessor 196 via data bus 204 to digital controller/timer circuit 206, where digital timers and counters establish the overall escape interval of the IMD 20 as well as various refractory, blanking and other timing windows for controlling the operation of peripheral components disposed within input/output circuit 186.

Digital controller/timer circuit 206 is preferably coupled to sensing circuitry, including sense amplifier 216, peak sense and threshold measurement unit 218 and comparator/threshold detector 220. Circuit 206 is further preferably coupled to electrogram (EGM) amplifier 222 for receiving amplified and processed signals sensed by lead 162. Sense amplifier 216 amplifies sensed electrical cardiac signals and provides an amplified signal to peak sense and threshold measurement circuitry 218, which in turn provides an indication of peak sensed voltages and measured sense amplifier threshold voltages on multiple conductor signal path 224 to digital controller/timer circuit 206. An amplified sense amplifier signal is also provided to comparator/threshold detector 220. By way of example, sense amplifier 216 may correspond to that disclosed in U.S. Pat. No. 4,379,459 to Stein, hereby incorporated by reference herein in its entirety.

The electrogram signal provided by EGM amplifier 222 is employed when IMD 20 is being interrogated by an external programmer to transmit a representation of a cardiac analog electrogram. See, for example, U.S. Pat. No. 4,556,063 to Thompson et al., hereby incorporated by reference herein in its entirety. Output pulse generator 226 provides amplified pacing stimuli to patient's heart 18 through coupling capacitor 228 in response to a pacing trigger signal provided by digital controller/timer circuit 206 each time either (a) the escape interval times out, (b) an externally transmitted pacing command is received, or (c) in response to other stored commands as is well known in the pacing art. By way of example, output amplifier 226 may correspond generally to an output amplifier disclosed in U.S. Pat. No. 4,476,868 to Thompson, hereby incorporated by reference herein in its entirety.

The specific embodiments of sense amplifier 216, output pulse generator 226 and EGM amplifier 222 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 18.

In some preferred embodiments of the present invention, IMD 20 may operate in various non-rate-responsive modes, including, but not limited to, DDD, DDI, VVI, VOO and VVT modes. In other preferred embodiments of the present invention, IMD 20 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 20 may be programmably configured to operate so that it varies the rate at which it delivers stimulating pulses to heart 18 in response to one or more selected sensor outputs being generated. Numerous pacemaker features and functions not explicitly mentioned herein may be incorporated into IMD 20 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 20 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 10:
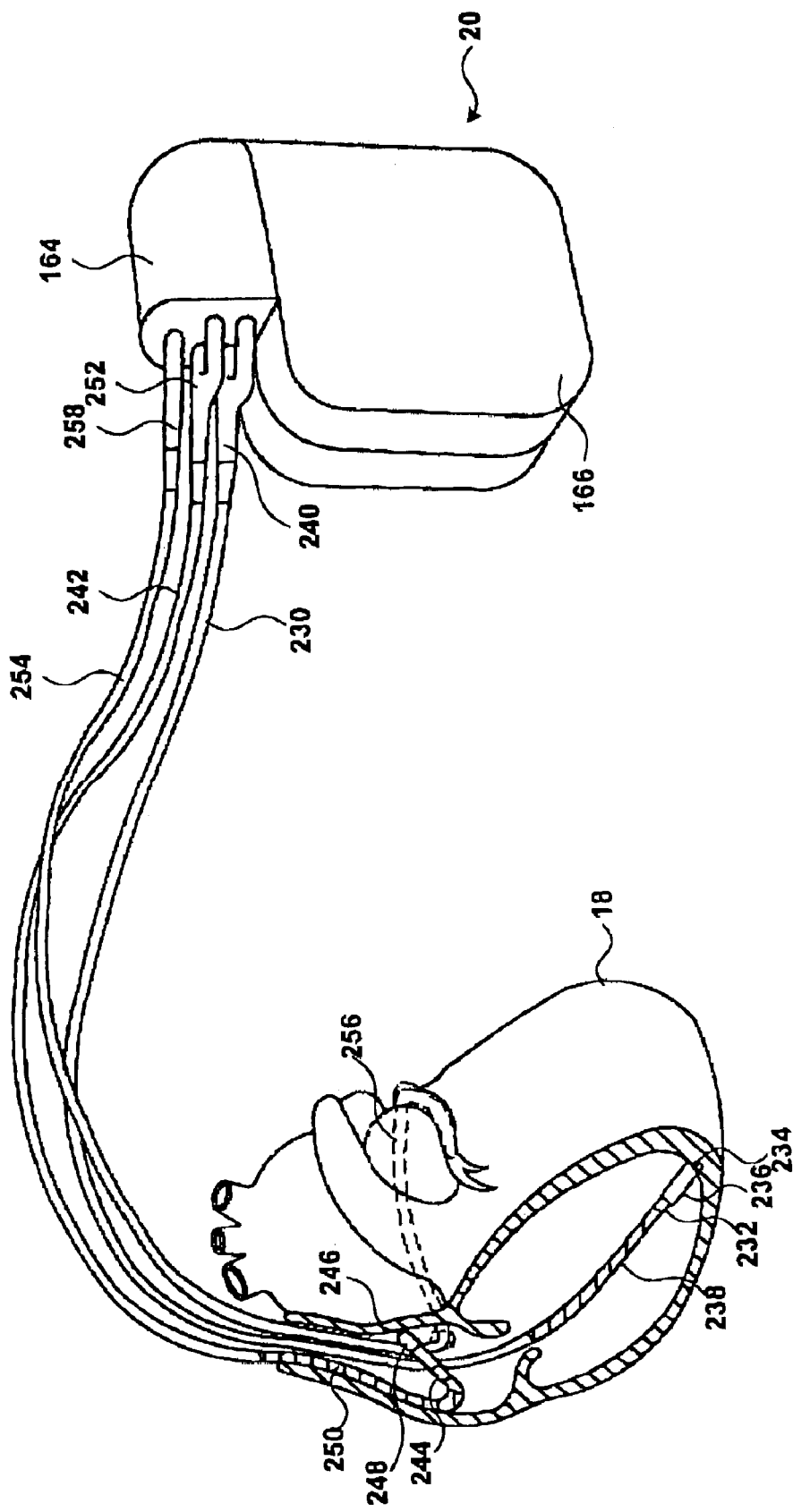
FIG. 10 shows a pacemaker-cardioverter-defibrillator located in and near a heart.
Figure 11:
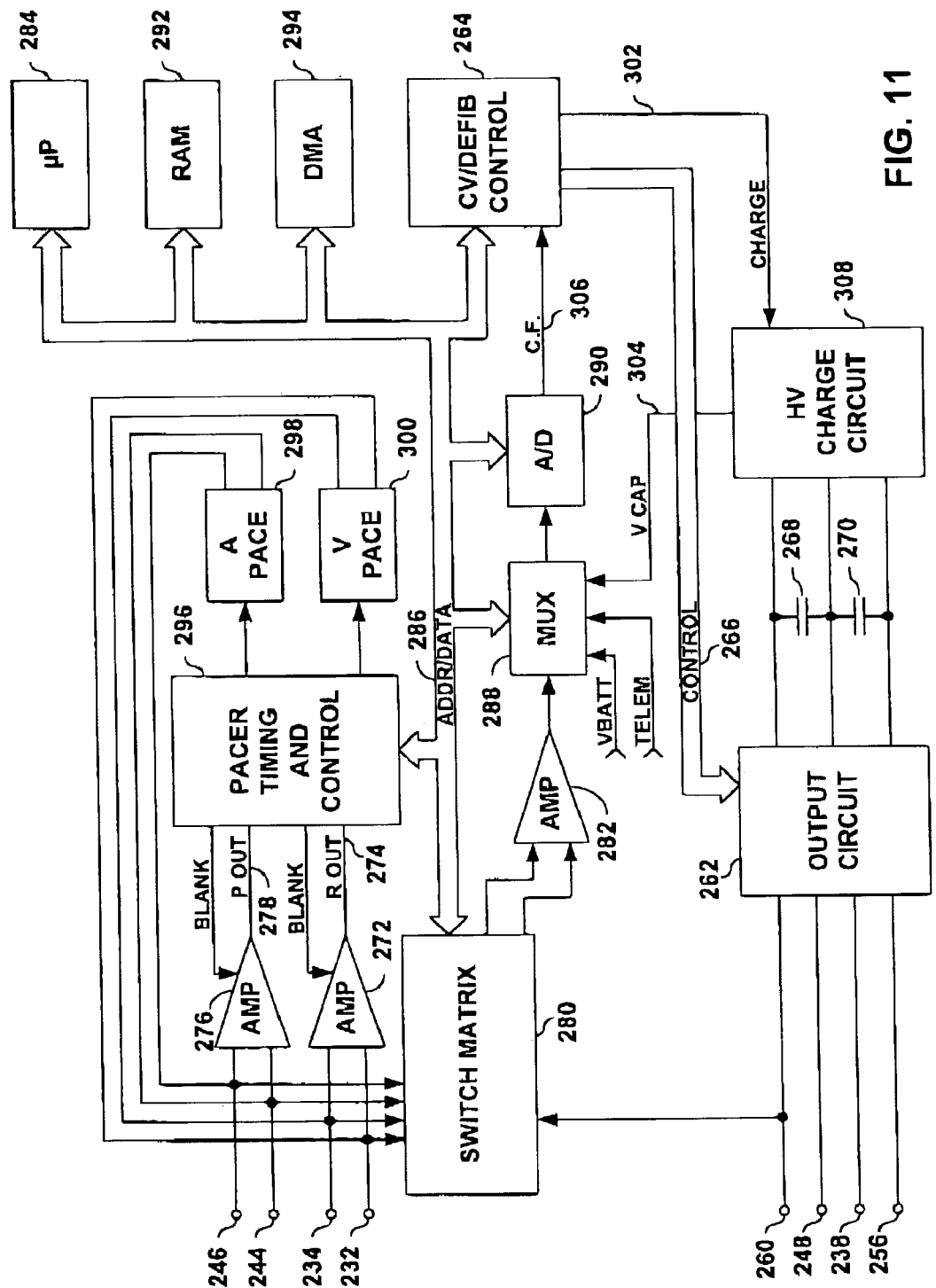
FIG. 11 is a functional schematic diagram of one embodiment of an implantable medical device.

FIGS. 10 and 11 illustrate one embodiment of IMD 20 and a corresponding lead set of the present invention, where IMD 20 is a PCD. In FIG. 10, the ventricular lead takes the form of leads disclosed in U.S. Pat. Nos. 5,099,838 and 5,314,430 to Bardy, and includes an elongated insulative lead body 230 carrying three concentric coiled conductors separated from one another by tubular insulative sheaths. Located adjacent the distal end of lead 230 are ring electrode 232, extendable helix electrode 234 mounted retractably within insulative electrode head 236 and elongated coil electrode 238. Each of the electrodes is coupled to one of the coiled conductors within lead body 230. Electrodes 232 and 234 are employed for cardiac pacing and for sensing ventricular depolarizations. At the proximal end of the lead is bifurcated connector 240 which carries three electrical connectors, each coupled to one of the coiled conductors. Elongated coil electrode 238, which is a defibrillation electrode 238, may be fabricated from platinum, platinum alloy or other materials known to be usable in implantable defibrillation electrodes and may be about 5 cm in length.

The atrial/SVC lead shown in FIG. 10 includes elongated insulative lead body 242 carrying three concentric coiled conductors separated from one another by tubular insulative sheaths corresponding to the structure of the ventricular lead. Located adjacent the J-shaped distal end of the lead are ring electrode 244 and extendable helix electrode 246 mounted retractably within an insulative electrode head 248. Each of the electrodes is coupled to one of the coiled conductors within lead body 242. Electrodes 246 and 244 are employed for atrial pacing and for sensing atrial depolarizations. Elongated coil electrode 250 is provided proximal to electrode 244 and coupled to the third conductor within lead body 242. Electrode 250 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 252 carrying three electrical connectors, each coupled to one of the coiled conductors.

The coronary sinus lead shown in FIG. 10 assumes the form of a coronary sinus lead disclosed in the above cited '838 patent issued to Bardy, and includes elongated insulative lead body 254 carrying one coiled conductor coupled to an elongated coiled defibrillation electrode 256. Electrode 256, illustrated in broken outline in FIG. 10, is located within the coronary sinus and great vein of the heart. At the proximal end of the lead is connector plug 258 carrying an electrical connector coupled to the coiled conductor. Elongated coil defibrillation electrode 254 may be about 5 cm in length.

IMD 20 is shown in FIG. 10 in combination with leads 230, 242 and 254, and lead connector assemblies 240, 252 and 258 inserted into connector module 164. Optionally, insulation of the outward facing portion of housing 166 of IMD 20 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 166 serves as a subcutaneous defibrillation electrode to defibrillate either the atria or ventricles. Lead configurations other that those shown in FIG. 10 may be practiced in conjunction with the present invention, such as those shown in U.S. Pat. No. 5,690,686 to Min et al., hereby incorporated by reference herein in its entirety.

FIG. 11 is a functional schematic diagram of one embodiment of IMD 20 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 20 is provided with an electrode system. If the electrode configuration of FIG. 10 is employed, the correspondence to the illustrated electrodes is as follows. Electrode 260 in FIG. 11 includes the uninsulated portion of the housing of IMD 20. Electrodes 260, 248, 256 and 238 are coupled to high voltage output circuit 262, which includes high voltage switches controlled by CV/defib control logic 264 via control bus 266. Switches disposed within circuit 262 determine which electrodes are employed and which electrodes are coupled to the positive and negative terminals of a capacitor bank (which includes capacitors 268 and 270) during delivery of defibrillation pulses.

Electrodes 232 and 234 are located on or in the ventricle of the patient and are coupled to the R-wave amplifier 272, which preferably takes the form of an automatic gain controlled amplifier providing an adjustable sensing threshold as a function of the measured R-wave amplitude. A signal is generated on R-out line 274 whenever the signal sensed between electrodes 232 and 234 exceeds the present sensing threshold.

Electrodes 244 and 246 are located on or in the atrium of the patient and are coupled to the P-wave amplifier 276, which preferably also takes the form of an automatic gain controlled amplifier providing an adjustable sensing threshold as a function of the measured P-wave amplitude. A signal is generated on P-out line 278 whenever the signal sensed between electrodes 244 and 246 exceeds the present sensing threshold. The general operation of R-wave and P-wave amplifiers 272 and 278 may correspond to that disclosed in U.S. Pat. No. 5,117,824 to Keimel et al., hereby incorporated by reference herein in its entirety.

Switch matrix 280 is used to select which of the available electrodes are coupled to wide band (0.5–200 Hz) amplifier 282 for use in digital signal analysis. Selection of electrodes is controlled by microprocessor 284 via data/address bus 286, which selections may be varied as desired. Signals from the electrodes selected for coupling to bandpass amplifier 282 are provided to multiplexer 288, and thereafter converted to multi-bit digital signals by A/D converter 290, for storage in random access memory 292 under control of direct memory access circuit 294. Microprocessor 284 may employ digital signal analysis techniques to characterize the digitized signals stored in random access memory 292 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 296 preferably includes programmable digital counters which control the basic time intervals associated with DDD, VVI, DVI, VDD, AAI, DDI and other modes of single and dual chamber pacing well known to the art. Circuitry 296 also preferably controls escape intervals associated with anti-tachyarrhythmia pacing in both the atrium and the ventricle, employing any anti-tachyarrhythmia pacing therapies known to the art.

Intervals defined by pacing circuitry 296 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 284, in response to stored data in memory 292 and are communicated to pacing circuitry 296 via address/data bus 286. Pacer circuitry 296 also determines the amplitude of the cardiac pacing pulses under control of microprocessor 284.

During pacing, escape interval counters within pacer timing/control circuitry 296 are reset upon sensing of R-waves and P-waves as indicated by a signals on lines 274 and 278, and in accordance with the selected mode of pacing on time-out trigger generation of pacing pulses by pacer output circuitry 298 and 300, which are coupled to electrodes 244, 246, 232 and 234. Escape interval counters are also reset on generation of pacing pulses and thereby control the basic timing of cardiac pacing functions, including anti-tachyarrhythmia pacing. The durations of the intervals defined by escape interval timers are determined by microprocessor 284 via data/address bus 286. The value of the count present in the escape interval counters when reset by sensed R-waves and P-waves may be used to measure the durations of R—R intervals, P—P intervals, P-R intervals and R-P intervals, which measurements are stored in memory 292 and used to detect the presence of tachyarrhythmias.

Microprocessor 284 most preferably operates as an interrupt driven device, and is responsive to interrupts from pacer timing/control circuitry 296 corresponding to the occurrence of sensed P-waves and R-waves and corresponding to the generation of cardiac pacing pulses. Those interrupts are provided via data/address bus 286. Any necessary mathematical calculations to be performed by microprocessor 284 and any updating of the values or intervals controlled by pacer timing/control circuitry 296 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT application Ser. No. US92/02829, Publication No. WO92/8198, by Adams et al., and in the article "Automatic Tachycardia Recognition," by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 284 into the pacer timing and control circuitry 296, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 284 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 284 activates cardioversion/defibrillation control circuitry 264, which initiates charging of high voltage capacitors 268 and 270 via charging circuit 308, under the control of high voltage charging control line 302. The voltage on the high voltage capacitors is monitored via VCAP line 304, which is passed through multiplexer 288 and in response to reaching a predetermined value set by microprocessor 184, results in generation of a logic signal on Cap Full (CF) line 306 to terminate charging. Thereafter, timing of the delivery of the defibrillation or cardioversion pulse is controlled by pacer timing/control circuitry 296. Following delivery of the fibrillation or tachycardia therapy microprocessor 184 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 11, delivery of cardioversion or defibrillation pulses is accomplished by output circuit 262 under the control of control circuitry 264 via control bus 266. Output circuit 262 determines whether a monophasic or biphasic pulse is delivered, the polarity of the electrodes and which electrodes are involved in delivery of the pulse. Output circuit 262 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 20 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

In some embodiments of the present invention in which IMD 20 is a pacemaker as described above with reference to FIGS. 6–11, processor 50 may generate a control signal to cause the pacemaker to adjust one or more pacing parameters as a function of the estimated stroke volume or cardiac output. Pacing parameters include, for example, pulse amplitude, pulse width, pulse rate, escape interval, or atrioventricular delay. Processor 50 may, for example, compare the estimated stroke volume or cardiac output to a threshold value stored in memory 54. If the stroke volume or cardiac output falls below the threshold, processor 50 may generate a control signal to cause pacemaker IMD 20 to modify a pacing parameter, to cause pacemaker IMD 20 to increase the pacing pulse amplitude for example, to increase stroke volume or cardiac output. The result of the modification by pacemaker IMD 20 may be apparent in the estimated stroke volume or cardiac output. Thus, processor 50 may use feedback to cause pacemaker IMD 20 to modify pacing parameters to maintain a target stroke volume or cardiac output.

Alternatively, processor 50 may cause pacemaker IMD 20 to iteratively change pacing parameters. The results of these changes may be reflected in the estimated stroke volume or cardiac output. Processor 50 may use this technique to determine an optimal set of pacing parameters, a set which yields the maximum stroke volume or cardiac output. This principle may similarly be used to determine the optimum pacing parameters for cardiac resynchronization therapy, or CRT.

Processor 50 may deliver the control signal to, for example, a microcomputer circuit 190, controller/timer circuit 206, microprocessor 284, or pacing/timing and control circuit 296 of pacemaker IMD 20, which is responsive to such a control signal. As mentioned above, processor may deliver this signal by a datalink or bus, or may deliver the control signal via RF telemetry utilizing RF telemetry circuit 57. IMD pacemaker 20 may receive such a signal via telemetry input to multiplexer 288 or RF transmitter and receiver circuit 210.

In some embodiments of the present invention, IMD 20 may comprise an implantable drug pump. Examples of implantable drug pumps include a number of SynchroMed™ pumps manufactured by and commercially available from Medtronic Inc. Pumps of this kind typically include self-sealing reservoirs that may be refilled by a needle and syringe, and need not be surgically removed when empty. The needle and syringe may also be used to drain a pump of one drug, flush the reservoir, and refilled the reservoir with a different drug. The invention is not limited to use with SynchroMed pumps, however, and may be adapted for use with other drug delivery devices.

Processor 50 may generate a control signal to cause drug pump IMD 20 to deliver a drug or modify the dosage of a delivered drug. Processor 50 may compare the estimated stroke volume or cardiac output to a threshold value stored in memory 54. If the stroke volume or cardiac output falls below the threshold, processor 50 may generate a control signal to cause drug pump IMD 20 to deliver a drug or increase the dosage of a drug that increases stroke volume or cardiac output. Drugs that increase stroke volume and cardiac output include positive inotropic cardiac drugs, such as digoxin. Positive inotropic cardiac drugs increase stroke volume and cardiac output by increasing the contractility of the heart, causing the heart to beat more forcefully and eject more blood per beat. The result of the delivering the drug or modifying the dosage may be apparent in the estimated stroke volume or cardiac output. Thus, processor 50 may use feedback to cause drug delivery IMD 20 to modify the delivery of drugs to maintain a target stroke volume or cardiac output.

The preceding specific embodiments are illustrative of the practice of the invention. It is to be understood, therefore, that other expedients known to those skilled in the art or disclosed herein may be employed without departing from the invention or the scope of the claims.

The invention further includes within its scope the methods of making and using the systems described above. These methods are not limited to the specific examples described above, but may be adapted to meet the needs of a particular patient. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. An implantable medical device comprising:
   an input circuit that receives a pressure signal representative of a pressure within a heart; and
   a processor that calculates a change in the pressure as a function of the pressure signal, and estimates a rate of blood flow from the heart as a function of the change in the pressure wherein the processor estimates a velocity-time integral as a function of the change in the pressure, and calculates the rate as a function of the velocity-time integral.

2. The device of claim 1, wherein the device is implanted in the upper chest of a patient.

3. The device of claim 1, wherein the rate is a stroke volume.

4. The device of claim 1, wherein the rate is a cardiac output.

5. The device of claim 1, further comprising a memory, wherein the processor stores the rate in the memory.

6. The device of claim 1, further comprising an input/output circuit coupled to the processor, the input/output circuit configured to exchange information between a person and the processor.

7. The device of claim 1, wherein the processor identifies a pressure value at a time of valve opening and a peak pressure value as a function of the pressure signal, and wherein the processor calculates the change in the pressure as a difference between the peak pressure value and the pressure value at the time of valve opening.

8. The device of claim 7, wherein the processor identifies a point of maximum positive slope of the pressure signal, and wherein the pressure value at the time of valve opening is a pressure value of the pressure signal at the point of maximum positive slope.

9. The device of claim 8, wherein the processor generates a differential signal that is representative of the first derivative of the pressure signal as a function of the pressure signal, and wherein the point of maximum positive slope of the pressure signal is a point of the pressure signal corresponding to a point of the differential signal where a maximum value of the differential signal occurs.

10. The device of claim 7, wherein the processor identifies a peak of the pressure signal, and wherein the peak pressure value is a pressure value at the peak.

11. The device of claim 1, wherein the processor estimates velocity data as a function of the change in pressure, and determines the rate as a function of the velocity data.

12. The device of claim 11, wherein the processor integrates the velocity data and determines the rate as a function of a result of the integration.

13. The device of claim 11, wherein the processor calculates a peak velocity as a function of the pressure signal, and estimates velocity data as a function of the peak velocity.

14. The device of claim 13, wherein the processor determines time data as a function of the pressure signal, and estimates the velocity data as a function of the peak velocity and the time data.

15. The device of claim 14, wherein the time data comprises a time of valve opening, a time of peak pressure and a time of valve closing, and
   wherein the processor estimates velocity data as a function of the peak velocity, the time of valve opening, the time of peak pressure and the time of valve closing.

16. The device of claim 15, wherein the pressure monitor identifies a point of maximum positive slope of the pressure signal, and
   wherein the time of valve opening is a time at the point of maximum positive slope.

17. The device of claim 16, wherein the processor generates a differential signal that is representative of the first derivative of the pressure signal as a function of the pressure signal, and
   wherein the point of maximum slope of the pressure signal is a point of the pressure signal corresponding to a point of the differential signal where a maximum value of the differential signal occurs.

18. The device of claim 15, wherein the processor identifies a peak of the pressure signal, and
   wherein the time of peak pressure is a time at which the peak occurs.

19. The device of claim 15, wherein the processor identifies a point of maximum negative slope of the pressure signal, and
   wherein the time of valve closing is a time at the point of maximum negative slope.

20. The device of claim 19, wherein the processor generates a differential signal that is representative of the first derivative of the pressure signal as a function of the pressure signal, and
   wherein the point of maximum negative slope of the pressure signal is a point of the pressure signal corresponding to a point of the differential signal where a minimum value of the differential signal occurs.

21. The device of claim 15, wherein the processor determines a time of peak velocity as a function of the time of peak pressure and estimates velocity data as a function of the time of valve opening, the time of peak velocity, the peak velocity and the time of valve closing.

22. The device of claim 1, wherein the processor determines time data as a function of the pressure signal, and estimates the rate as a function of the time data and the change in the pressure.

23. The device of claim 22, wherein the time data comprises a time of valve opening and a time of valve closing.

24. The device of claim 23, wherein the pressure monitor identifies a point of maximum positive slope of the pressure signal, and sets the time of valve opening as a time at the point of maximum positive slope.

25. The device of claim 24, wherein the processor generates a differential signal that is representative of the first derivative of the pressure signal as a function of the pressure signal, and wherein the point of maximum slope of the pressure signal is a point of the pressure signal corresponding to a point of the differential signal where a maximum value of the differential signal occurs.

26. The device of claim 23, wherein the processor identifies a point of maximum negative slope of the pressure signal, and sets the time of valve closing as a time at the point of maximum negative slope.

27. The device of claim 26, wherein the processor generates a differential signal that is representative of the first derivative of the pressure signal as a function of the pressure signal, and wherein the point of maximum negative slope of the pressure signal is a point of the pressure signal corresponding to a point of the differential signal where a minimum value of the differential signal occurs.

28. The device of claim 23, wherein the processor calculates a duration of a time period between the time of valve opening and the time of valve closing and estimates the rate as a function of the duration.

29. The device of claim 28, wherein the input circuit further receives an electrical activity signal, the electrical activity signal a function of electrical activity within the heart, and wherein the processor calculates a heart rate as a function of the electrical activity signal and determines the cardiac output as a function of the heart rate and the velocity-time integral.

* * * * *